(12) United States Patent
Lee et al.

(10) Patent No.: US 8,429,975 B2
(45) Date of Patent: Apr. 30, 2013

(54) SYSTEM AND METHOD FOR SIMULATING HIGH-INTENSITY PYROTECHNIC SHOCK

(75) Inventors: Chi Chin Lee, Riverside, CA (US); Chhour Meng Thong, Buena Park, CA (US); Mitchell Eugene West, Buena Park, CA (US); Raymond R. Slonena, Jr., Irvine, CA (US)

(73) Assignee: The Boeing Company, Chicago, IL (US)

( * ) Notice: Subject to any disclaimer, the term of this patent is extended or adjusted under 35 U.S.C. 154(b) by 97 days.

(21) Appl. No.: 13/092,116

(22) Filed: Apr. 21, 2011

(65) Prior Publication Data

US 2012/0271603 A1 Oct. 25, 2012

(51) Int. Cl.
*B06B 3/02* (2006.01)

(52) U.S. Cl.
USPC ........................................................... 73/663

(58) Field of Classification Search .................. None
See application file for complete search history.

(56) References Cited

U.S. PATENT DOCUMENTS

| | | | |
|---|---|---|---|
| 3,597,960 A * | 8/1971 | Otera et al. | 73/12.04 |
| 5,003,811 A | 4/1991 | Shannon | |
| 5,400,640 A | 3/1995 | Stuckey | |
| 5,565,626 A | 10/1996 | Davie | |
| 6,502,464 B1 * | 1/2003 | Hobbs | 73/663 |
| 6,553,839 B2 * | 4/2003 | Board | 73/663 |
| 7,464,597 B1 | 12/2008 | Lee et al. | |
| 2009/0048814 A1 | 2/2009 | Lee et al. | |

OTHER PUBLICATIONS

International Search Report, PCT/US2012/027987, dated Jul. 5, 2012.

* cited by examiner

*Primary Examiner* — Robert R Raevis
(74) *Attorney, Agent, or Firm* — Novatech IP Law

(57) ABSTRACT

A system for simulating a pyrotechnic shock may include an electrical power amplifier, a shaker, and a resonance beam. The electrical power amplifier may be configured to amplify a transient signal waveform representing a desired shock response spectrum (SRS). The shaker may be configured to generate a shock pulse in response to the amplified signal waveform. The resonance beam may be mounted to the shaker and may be configured to magnify the shock pulse.

19 Claims, 11 Drawing Sheets

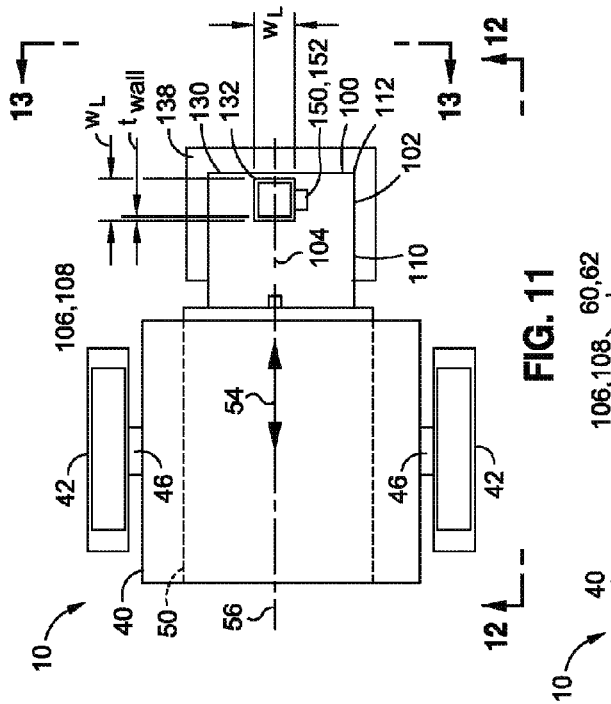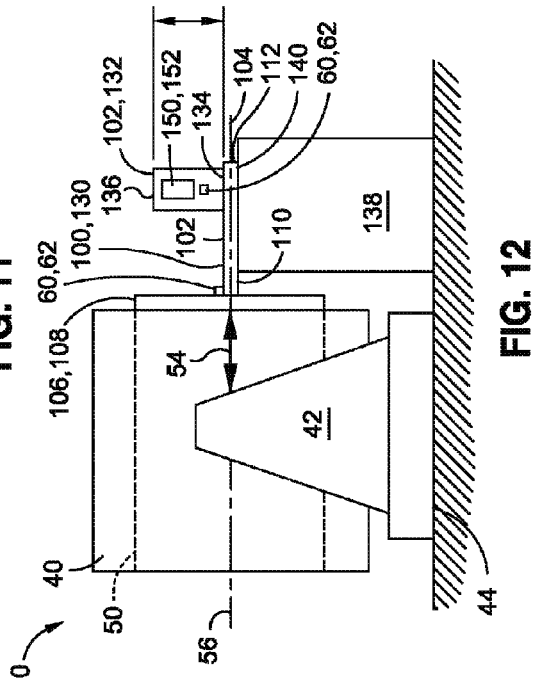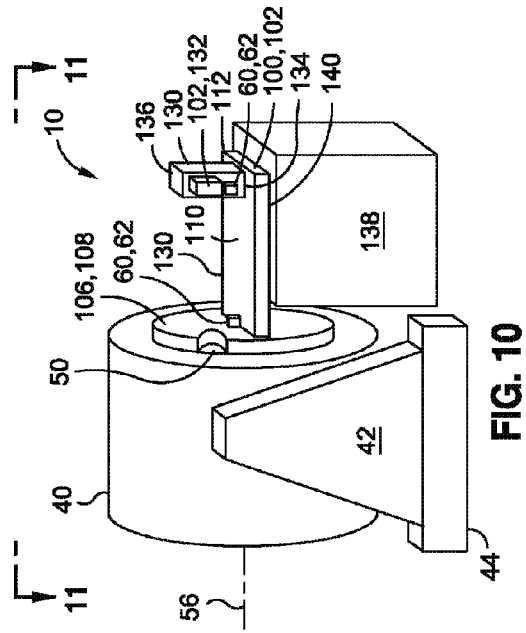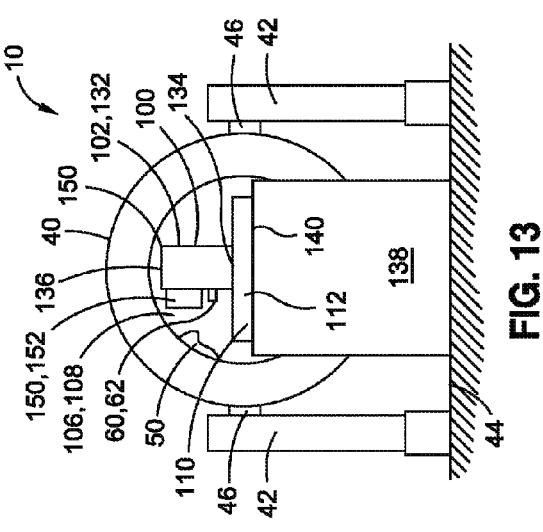

SYSTEM AND METHOD FOR SIMULATING HIGH-INTENSITY PYROTECHNIC SHOCK

FIELD

The present disclosure relates generally to shock testing and, more particularly, to systems and methods for simulating high intensity pyrotechnic shock in a component or article under test.

BACKGROUND

Spacecraft such as communications satellites may be subjected to several discrete shock events during launch into orbit. For example, a spacecraft carried by a launch vehicle may be subjected to shock during separation of the boosters from the launch vehicle and during staging of the launch vehicle. The spacecraft may also be subjected to shock during separation of the spacecraft from the launch vehicle and during deployment of subsystems such as solar panels once the spacecraft is inserted into orbit.

Pyrotechnic or explosive materials are used extensively in space launches to facilitate the above-mentioned separation and deployment events. The release of explosive energy during a separation or deployment event may result in the generation of a shock pulse of relatively short duration and high magnitude. For example, the shock pulse may have a duration of from 50 microseconds to no more than 20 milliseconds. In addition, the shock pulse may have a frequency range of up to 1,000,000 Hz and a peak amplitude (e.g., acceleration) of up to 300,000 g's. Such relatively high intensity shock pulses may be transmitted to sensitive components and instrumentation that may be mounted to the spacecraft and the launch vehicle.

In order to ensure that such components are capable of withstanding high-intensity shock pulses during a launch, individual components are typically subjected to qualification testing in a laboratory environment or other controlled environment. During qualification testing, a component may be subjected to a shock pulse simulating the pyrotechnic shock expected to occur in the service environment (e.g., on the launch vehicle). The pyrotechnic shock to be simulated is typically characterized using a specified or desired shock response spectrum (SRS). The desired SRS may be developed by measuring the response (e.g., the accelerations) of simulated or actual system structure to pyrotechnic shock using live ordnance. For example, a desired SRS may be developed representing the pyrotechnic shock transmitted to a communications satellite mounted on a payload attach fitting of a launch vehicle. The desired SRS may envelope the composite of all the pyrotechnic shock(s) that occur during a flight sequence. For example, the desired SRS may include the shock that occurs during separation of the rocket motors from the launch vehicle, the shock during separation of the fairing from the launch vehicle, the shock during detonation of a pyrotechnic bolt cutter to release a clamp band securing the satellite to the payload attach fitting to allow the satellite to separate from the launch vehicle, and other shock events.

Existing systems and methods for simulating pyrotechnic shock during qualification testing of a component include the use of measured quantities of ordnance in a laboratory environment. The ordnance may be attached to a structure upon which the component or a mass model of the component may be mounted. The ordnance may be detonated in an attempt to generate a shock pulse that results in an acceleration response in the structure that duplicates the desired SRS. Unfortunately, shock pulses generated using such method may be imprecise due to difficulty in quantifying the potential energy contained in a measured quantity of ordnance (i.e., explosive) charge. In addition, shock pulses generated from live ordnance may be difficult to control resulting in time-consuming repeat testing using different quantities of live ordnance on a trial-and-error basis until achieving an acceleration response that is within acceptable limits of the desired SRS.

Furthermore, because the desired SRS may envelope several different shock events with varying frequency content, testing using live ordnance may result in over-testing of a test article which may result in damage to expensive test hardware and requiring failure analysis, and repair, rework, or redesign of the hardware followed by re-testing. Reducing the quantity of ordnance to avoid over-testing may result in under-testing of the test article wherein the shock magnitudes are less than the levels specified for the qualification test. A further drawback associated with the use of explosive materials for qualification testing is that elaborate measures may be required for safe handling and storage of the materials.

Existing systems for simulating pyrotechnic shock may also include the use of mechanical impact to generate a shock pulse in a structure to which a component under test may be mounted. Unfortunately, the mechanical impact method presents challenges in accurately reproducing a desired acceleration in the structure from one mechanical impact to another. In addition, the mechanical impact method may result in mechanical ringing or residual shock response in the structure at the termination of the primary shock pulse. Such mechanical ringing may not otherwise occur in the actual flight structure due to absorption, dampening, attenuation, or distribution of shock that may be available in the actual flight structure. In this regard, such mechanical ringing that may occur in the impact method may result in inaccurate simulation of the pyrotechnic shock.

As can be seen, there exists a need in the art for a system and method for accurately simulating high-intensity pyrotechnic shock with a desired SRS that envelopes several different shock events with varying frequency content. Furthermore, there exists a need in the art for a system and method for simulating high-intensity pyrotechnic shock which can be precisely controlled with excellent repeatability and which is low in cost.

BRIEF SUMMARY

The above-described needs associated with simulation of high-intensity pyrotechnic shock are specifically addressed and alleviated by the present disclosure which, in an embodiment, provides a system for simulating a pyrotechnic shock. The system may include an electrical power amplifier, a shaker, and a resonance beam. The electrical power amplifier may be configured to amplify a transient signal waveform representing a desired shock response spectrum (SRS). The shaker may be configured to generate a shock pulse in response to the amplified signal waveform. The resonance beam may be mounted to the shaker and may be configured to magnify the shock pulse.

In a further embodiment, disclosed is a system for simulating a pyrotechnic shock represented by a desired shock response spectrum (SRS) having at least one knee frequency and a tolerance band. The system may comprise an electrical power amplifier configured to amplify a transient signal waveform representing the desired SRS. The system may further include an electrodynamic shaker having an armature and a reference axis. The shaker may be configured to generate a shock pulse in response to the amplified signal waveform. The shock pulse may be oriented substantially parallel to the reference axis. The system may further include a resonance beam that may be mounted to the armature. The resonance beam may be configured to magnify the shock pulse such that at least one location on the resonance beam has an absolute peak acceleration that is substantially equivalent to the acceleration at the knee frequency.

Also disclosed is a method of simulating a pyrotechnic shock having a desired shock response spectrum (SRS). The method may include the step of generating a shock pulse using a shaker having a resonance beam mounted thereto. The method may additionally include exciting the resonance beam in response to the shock pulse. The method may also include magnifying the shock pulse in at least one location on the resonance beam in response to excitation of the resonance beam.

In a further embodiment, disclosed is a method of simulating a pyrotechnic shock. The pyrotechnic shock may have a desired shock response spectrum (SRS) including a knee frequency and an acceleration corresponding to the knee frequency. The method may comprise the steps of generating a transient signal waveform representing the desired SRS and amplifying the signal waveform. The amplified signal waveform may be applied to an electrodynamic shaker having a resonance beam mounted thereto. The method may include generating a shock pulse at the shaker in response to the amplified signal waveform. The shock pulse may be oriented substantially parallel to the reference axis. The method may further include exciting the resonance beam in response to generation of the shock pulse, and magnifying the shock pulse in the resonance beam in response to excitation of the resonance beam.

The method may additionally include measuring a peak acceleration at a location on the resonance beam in response to magnification of the shock pulse, and calculating a simulated SRS based on the measured peak acceleration. The method may also include adjusting at least one test variable until an absolute peak acceleration of the simulated SRS is substantially equivalent to the acceleration corresponding to the knee frequency. The test variable may include adjusting the location on the resonance beam where the acceleration is measured. The test variable may also include adjusting the configuration of the resonance beam.

The features, functions and advantages that have been discussed can be achieved independently in various embodiments of the present disclosure or may be combined in yet other embodiments, further details of which can be seen with reference to the following description and drawings below

BRIEF DESCRIPTION OF THE DRAWINGS

These and other features of the present disclosure will become more apparent upon reference to the drawings wherein like numerals refer to like parts throughout and wherein:

FIG. 10 is a perspective illustration of an embodiment of the system wherein the resonance beam is configured as an L-beam comprising an axial beam and a lateral element;

FIG. 11 is top view illustration of the system taken along line 11-11 of FIG. 10 and illustrating the L-beam mounted to the shaker and the lateral element illustrated as a square tube;

FIG. 12 is side view illustration of the system taken along line 12-12 of FIG. 11 and illustrating the L-beam slidably supported on a beam support;

FIG. 13 is side view illustration of the system taken along line 13-13 of FIG. 11 and illustrating the L-beam slidably supported on the beam support and the shock pulse imparted to the axial beam;

DETAILED DESCRIPTION

Figure 1:
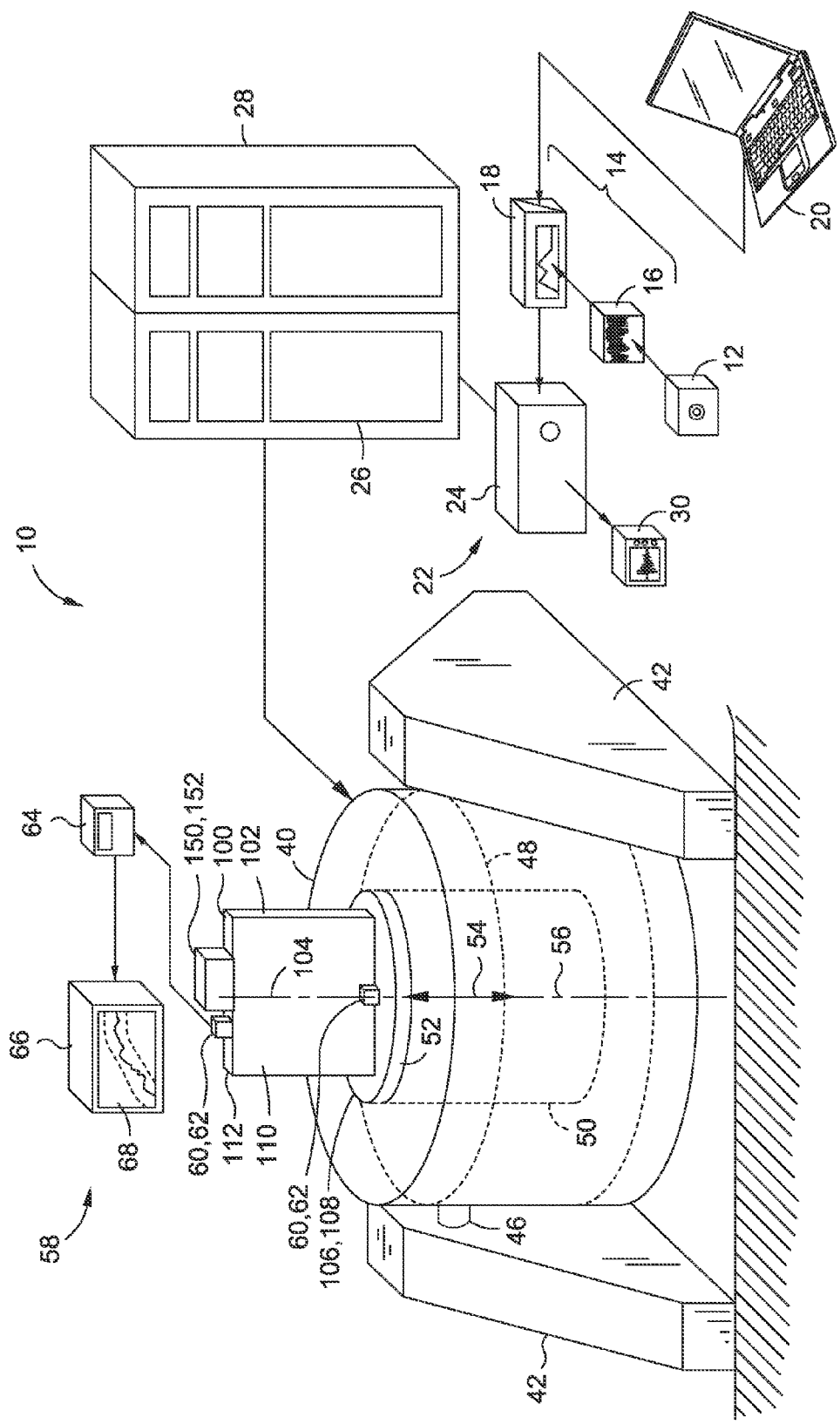
FIG. 1 is an illustration of a schematic diagram of an embodiment of a system for simulating pyrotechnic shock in a test article and including a shaker and a resonance beam for magnifying a shock pulse generated by the shaker.

Referring now to the drawings wherein the showings are for purposes of illustrating preferred and various embodiments of the disclosure, shown in FIG. 1 is an illustration of an embodiment of a system 10 for simulating pyrotechnic shock. The system 10 may include an electrodynamic shaker 40 and a test fixture 10 comprising a resonance beam 102 mounted to the shaker 40 for magnifying a shock pulse 54 generated by the shaker 40. The shock pulse may be generated in response to an amplified transient signal waveform provided to the shaker 40 by an electrical power amplifier 28. Advantageously, due to the mechanical advantage provided by the resonance beam 102, a precisely controlled, high intensity shock may be applied to a test article 150 mounted to the resonance beam 102.

As shown in FIG. 1, the system 10 may include a pulse signal generator 12 configured to generate the transient signal waveform of a desired magnitude and duration for achieving a desired pulse profile in the shock pulse 54 generated by the shaker 40. The transient signal may have a duration on the order of microseconds to milliseconds as may be desired for simulating pyrotechnic shock. In an embodiment, the transient signal may have a duration of less than 20 milliseconds although the transient signal may be provided in any duration. The transient signal may be provided in a variety of different waveforms including, but not limited to, a sine wave, a saw tooth wave, a square wave, a triangle wave, and other waveforms or combination of waveforms.

A signal conditioning device 14 may be included in the system 10 to shape or manipulate the transient signal waveform generated by the signal generator 12. The signal conditioning device 14 may include an analog filter 16 which may be configured as a ⅓ octave filter having sliders (e.g., variable resistors) for adjusting the magnitude of the signal at ⅓ octave frequency intervals or at other frequency intervals. The signal conditioning device 14 may also include a digital filter 18 which may receive the transient signal waveform from the analog filter 16. The digital filter 18 may be configured as a ⅓ octave digital filter 18 although the digital filter 18 may allow for adjusting the transient signal at different frequency increments other than ⅓ octave increments.

The digital filter 18 may include digital sliders (not shown) which may be displayed on a display of a host computer 20 that may be coupled to the digital filter 18. In this manner, the digital filter 18 may facilitate the manipulation of the output level of the transient signal or shaping the spectrum of the transient signal at different frequencies. For example, the digital filter 18 may allow for adjusting the transient signal output levels in ¼ dB increments at one or more frequencies as a means to control the profile of the shock pulse 54. The host computer 20 may provide a means to save the settings of a given transient signal spectrum for recall and use at a later time. The signal conditioning device 14 may function as a signal amplifier and may provide a means to adjust the gain of the transient signal such as in ½ dB increments or in other suitable increments.

In this regard, the signal conditioning device 14 may provide a means for increasing the dynamic range of the shock pulse 54 generated by the shaker 40. In addition, the adjustability of the analog 16 and digital filters 18 provides a means for controlling a shock response spectrum (SRS) of the resonance beam 102 such that the SRS of the resonance beam 102 may be maintained within a relatively narrow tolerance band to minimize or prevent over-testing of the test equipment. In this manner, the signal conditioning device 14 improves the precision, control and repeatability of shock testing.

Referring still to FIG. 1, the system 10 may additionally include a control unit 22 which may be coupled to the power amplifier 28 and which may receive the transient signal waveform from the digital filter 18. The control unit 22 may be configured to facilitate clipping of relatively high frequencies in the transient signal waveform. In addition, the control unit 22 may be configured to smooth the transient signal waveform to prevent tripping (i.e., deactivating) the power amplifier 28 or the shaker 40 as may occur with an abrupt or rapid ramp-up in the magnitude of the transient signal waveform.

A voltage monitoring device 30 such as an oscilloscope or similar device may also optionally be included with the system 10. The monitoring device 30 may be coupled to a mixer/clipper or master gain control 24 and may provide a means to visually monitor the magnitude of the voltage in the transient signal transmitted to the power amplifier 28. The monitoring device 30 may allow a user to monitor the shape of the transient signal and the voltage levels being transmitted to the power amplifier 28. In this manner, a user may adjust the transient signal as appropriate to prevent the transmission of excessive power to the power amplifier 28 and avoid over-testing.

Also included in the system 10 is the electrical power amplifier 28 which may include a direct current generator 26 to provide direct current to a field coil 48 of the shaker 40. The direct current may create a static magnetic field surrounding a movable driver coil or armature 50 of the shaker 40. In an embodiment, the direct current generator 26 may be configured to generate a direct current of up to approximately 300 amperes or more. In addition, the power amplifier 28 may amplify the transient signal waveform and may provide alternating current to the armature 50 causing the armature 50 to move axially along the reference axis 56 of the shaker 40 in correspondence with the frequencies and magnitudes of the alternating current. In an embodiment, the power amplifier 28 may generate an alternating current of up to approximately 500 amperes or greater. The power amplifier 28 may preferably be configured to amplify the transient signal with minimal distortion.

As shown in FIG. 1, the shaker 40 may be communicatively coupled to the power amplifier 28. The shaker 40 may be supported by a pair of stanchions 42 mounted on a rigid, non-movable surface of relatively large mass such as a concrete floor 44. The shaker 40 may be pivotally mounted to the stanchions 42 by a pair of trunnions 46 extending between the shaker 40 and the stanchion 42 on each side of the shaker 40. Advantageously, the pivotable mounting of the shaker 40 facilitates adjusting the shaker 40 and test fixture 10 into different orientations and positions to achieve different responses in the resonance beam as described below. The shaker 40 includes the field coil 48 which may surround the armature 50. The armature 50 may move axially along the reference axis 56 of the shaker 40 in response to application of the amplified signal waveform generated by the power amplifier 28.

The test fixture 10 may comprise the resonance beam 102 mounted to the shaker 40. The resonance beam 102 may have a base portion 106 directly attached to the armature 50 such that the resonance beam 102 and armature 50 move in unison.

Advantageously, the resonance beam 102 is configured to magnify the shock pulse 54 by excitation of the resonance beam 102 into one or more resonant modes as described in greater detail below. For example, the resonance beam 102 may be configured to resonate predominantly in a longitudinal mode, in a bending or flexural mode, and/or in a torsional mode, or in other modes or combinations thereof. The mode of resonance or excitation of the resonance beam 102 may be a function of the configuration of the resonance beam 102 geometry and the orientation and positioning of the resonance beam 102 on the shaker 40 as described below.

Figure 15:
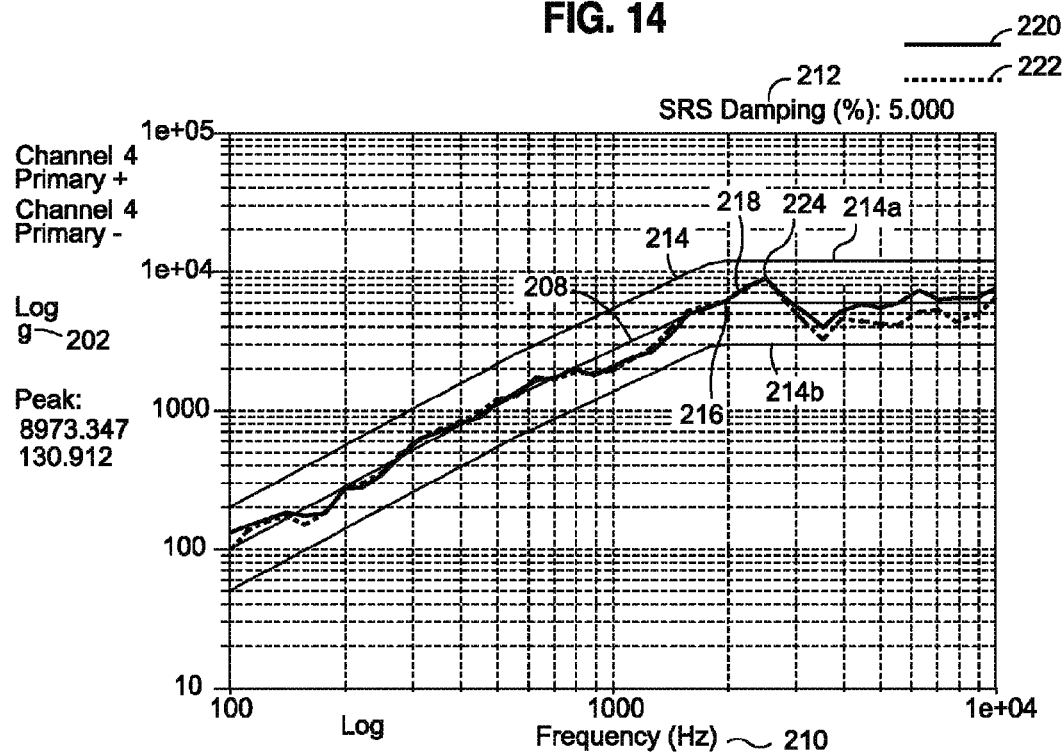
FIG. 15 is a simulated SRS based on the acceleration time history of FIG. 14.

An article under test 150 may be mounted to the resonance beam 102 at a location that produces a desired magnification of the shock pulse 54. In an embodiment, the magnification of the shock pulse 54 is preferably such that for at least one location, the resonance beam 102 exhibits a measured peak acceleration 206 that is greater than the measured peak acceleration 206 at a base portion 106 of the resonance beam 102. In an embodiment, the resonance beam 102 is preferably configured such that at least one location on the resonance beam 102 exhibits a simulated SRS 218 (FIG. 15) that is substantially similar to a desired SRS 208 (FIG. 15). In a preferred embodiment, the resonance beam 102 is configured such that at least one location on the resonance beam 102 has an absolute peak acceleration that is substantially equivalent to the acceleration corresponding to a knee frequency 216 (FIG. 15) of the desired SRS 208. The knee frequency 216 of an SRS corresponds to the dominant frequency of the service environment (i.e., the structure) in response to pyrotechnic shock.

The desired SRS 208 (FIG. 15) may represent the acceleration response to pyrotechnic shock from live ordnance (not shown) in an actual service environment. For example, the desired SRS 208 may represent the response of actual or simulated flight structure (not shown) to pyrotechnic shock from live ordnance measured near the actual mounting location of an article (e.g., a component or a subassembly). The desired SRS 208 may be based upon the acceleration time history 200 (FIG. 14) of the service environment subjected to pyrotechnic shock from live ordnance. More specifically, the desired SRS 208 may be calculated from the measured peak acceleration 206 (FIG. 14) of the acceleration time history 200. The desired SRS 208 is typically specified with a tolerance band 214 (FIG. 15). As shown in FIG. 15, the tolerance band 214 includes upper and lower limits 214a, 214b (e.g., +/−3 dB, +/−6 dB, +9/−6 dB) which may be determined based upon program requirements.

The desired SRS 208 (FIG. 15) represents a measure of the severity of a shock pulse or the damage potential of the shock pulse to a plurality of single-degree-of-freedom mass spring systems (not shown) each having a different resonant frequency. The desired SRS 208 may be expressed in terms of maximum absolute acceleration response which is referred to as the maximax and defined as the maximum of both the maximum positive and maximum negative accelerations. The calculation of the desired SRS 208 is based on a selected damping ratio which is typically 5 percent although a desired SRS 208 may be determined using a different damping ratio. The desired SRS 208 may be provided to a shock testing facility as a test specification to which a test article 150 (i.e., a component or subassembly) is to be subjected for one or more purposes such as development testing, qualification testing, flight acceptance testing, or for other purposes.

Referring still to FIG. 1, the system 10 may include an acceleration sensor 60 preferably mounted on the resonance beam 102 in close proximity to the article under test 150 for measuring, recording, and/or storing shock or acceleration response of the resonance beam 102 at a location. The acceleration sensor 60 may comprise an accelerometer 62 although the acceleration sensor 60 may be configured in an alternative embodiment including, but not limited to, strain gauges, velocity gauges, displacement devices, laser velocimeters, or other acceleration measurement devices. The accelerometer 62 may be a piezoelectric accelerometer or a piezoresistive accelerometer. The accelerometer 62 may be configured as a single axis accelerometer. More preferably, the accelerometer 62 is configured as a triaxial accelerometer for measuring acceleration in each of three mutually perpendicular axes. In this regard, one or more triaxial accelerometers 62 may be mounted to the resonance beam 102 during the process of identifying locations on the resonance beam having a desired magnification of the shock pulse. Accelerometers 62 may also be mounted to the resonance beam 102 during shock testing of a test article 150 after identifying resonance beam 102 locations having the desired magnification level.

The test article 150 may be subjected to shock testing for different purposes. For qualification testing, an article under test 150 is typically subjected to three shocks per direction (i.e., +/−) for each axis (i.e., x, y, z) of the test article 150 for a total of 18 shocks. During application of a shock pulse 54, the test article 150 is preferably oriented such that the active axis (i.e., the x-axis, y-axis, or z-axis) of the test article 150 is substantially parallel to the direction of the shock pulse 54 which, in FIG. 1, is substantially parallel to the reference axis 56 of the shaker 40. For flight acceptance testing, the quantity of shocks to which the article under test 150 is subjected may be reduced to a single shock in each direction (i.e., +/−) for each axis (i.e., x, y, z) for a total of 6 shocks although the test article 150 may be subjected to any number of shocks.

Referring still to FIG. 1, the system 10 may include a data acquisition system 58 for acquiring and processing acceleration data measured by the acceleration sensors 60 mounted to the resonance beam 102. In an embodiment, the data acquisition system 58 may include a signal conditioner 64. The signal conditioner 64 may provide power to the acceleration sensor 60 and may amplify an output signal of the acceleration sensor 60. The data acquisition system 58 may additionally include a data analyzer or shock spectrum analyzer 66 which may have a display 68 for visually displaying the results of a shock pulse imparted to the resonance beam 102. The shock spectrum analyzer 66 may display a simulated SRS 218 of the resonance beam 102 at a given location. In the display, the simulated SRS may be superimposed over the desired SRS with tolerance bands to provide a visual indication of the accuracy of the shock pulse in simulating a pyrotechnic shock.

Referring to FIGS. 2-5, shown is an embodiment of the system 10 wherein the resonance beam 102 is configured as an axial beam 110. The axial beam 110 has a base portion 106 and a free end 136 and a long axis 104 extending between the base portion 106 and the free end 136. The base portion 106 is mounted to the armature 50 such as by mechanically fastening the base portion 106 to the armature 50 although the base portion 106 may be welded to the armature 50 or attached in another manner. For example, the axial beam 110 and armature 50 may be formed as a unitary structure. In an embodiment, the base portion 106 may include an adapter plate 108 to facilitate mounting of the axial beam 110 to the armature 50. The base portion 106 may be disc-shaped and may be formed complementary to a circular shape of the armature 50. However, the adapter plate 108 may be provided in any one of a variety of alternative sizes and shapes. Regardless of the specific configuration of the base portion 106, the axial beam 110 is preferably mounted to the armature 50 such that the axial beam 110 and the armature 50 remain in continuous contact with one another for the duration of the shock pulse 54 and move as a unit in response to the shock pulse 54.

The long axis 104 of the axial beam 110 may be oriented substantially parallel to the reference axis 56. The reference axis 56 is the axis along which the armature 50 moves and is the predominant direction along which the shock pulse 54 is imparted to the axial beam 110. In an embodiment, the orientation and configuration of the axial beam 110 may be such that the shock pulse 54 excites the axial beam 110 into a predominantly longitudinal mode of excitation although the axial beam 110 may be excited into other modes including a flexural mode or in combinations of modes. When excited, the axial beam 110 may have anti-nodes (not shown) at locations of the axial beam 110 where magnification of the shock pulse 54 may occur. Such anti-node locations may increase or magnify the shock pulse energy. Conversely, the axial beam 110 may have nodes (not shown) at locations of reduced magnification or non-magnification. Such node locations may absorb the shock pulse energy.

Figure 2:
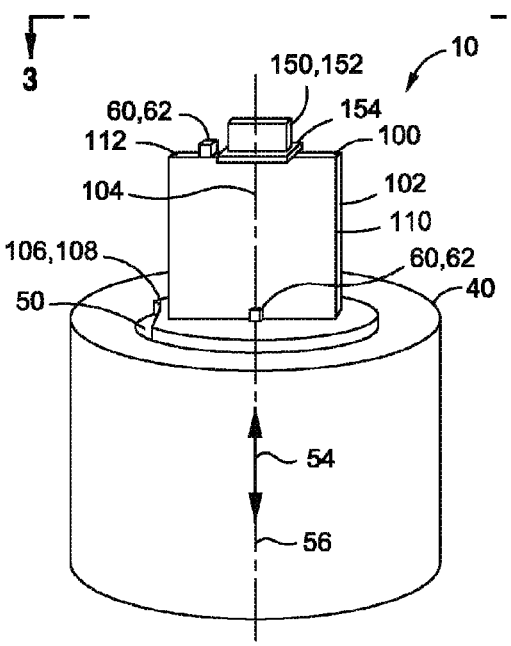
FIG. 2 is a perspective illustration of an embodiment of the system wherein the resonance beam is configured as an axial beam.

The test article 150 may be mounted at any location of the axial beam 110 and preferably at a location that provides a desired level of magnification of the shock pulse 54. For example, FIG. 2 illustrates the test article 150 mounted on a holding fixture 154 at the free end 112 of the axial beam 110 which may magnify the shock pulse 54 by a factor of two or more as described in greater detail below. The axial beam 110 may include at least one accelerometer 62 mounted to the axial beam 110 at a location proximate the test article 150. Another accelerometer 62 may be mounted to the axial beam 110 proximate the base portion 106 to measure acceleration response at the base portion 106 for comparison to the acceleration response of the axial beam 110 at the test article 150.

Figure 3:
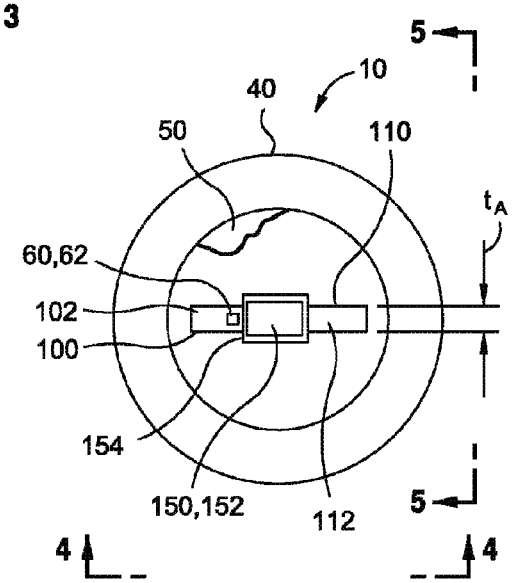
FIG. 3 is top view illustration of the system taken along line 3-3 of FIG. 2 and illustrating the axial beam mounted to the shaker.

FIG. 3 is a top view of the axial beam 110 mounted to the shaker 40 armature 50. Although the axial beam 110 is shown as being generally centered on the shaker 40, the axial beam 110 may be offset from the shaker 40 center. The axial beam 110 has a thickness $t_A$ that is preferably no greater than approximately one-half the width $w_A$ (FIG. 4) of the axial beam 110 although the axial beam 110 may have a thickness $t_A$ that is no greater than the width $w_A$ of the axial beam 110. The axial beam 110 may have an orthogonally shaped cross section such as the rectangular cross section shown. However, the axial beam 110 may have a square cross section (not shown). Furthermore, the axial beam 110 may have a non-orthogonal cross section of any shape or configuration. For example, the axial beam 110 may have a cross section that may be at least partially curved such as a circular cross section (not shown) resulting in a cylindrical shape of the axial beam 110. In this regard, the axial beam 110 may be provided in any one of a variety of cross sectional shapes which may produce different levels of magnification at different locations.

Figure 4:
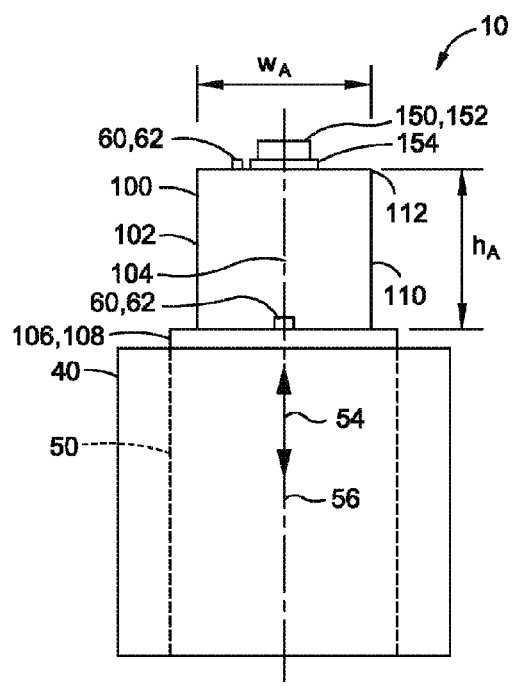
FIG. 4 is side view illustration of the system taken along line 4-4 of FIG. 3 and illustrating the shock pulse imparted to the axial beam.

FIG. 4 is a side view of the axial beam 110 mounted to the shaker 40 armature 50. The axial beam 110 may have a height $h_A$ measured parallel to the long axis 104 and a width $w_A$ measured perpendicular to the long axis 104. In an embodiment, the height $h_A$ of the axial beam 110 is greater than the width $w_A$ of the axial beam 110. For example, the height $h_A$ of the axial beam 110 may be at least twice the width $w_A$. In a further embodiment, the height $h_A$ may be approximately 2 to 5 times greater than the width $w_A$ although the height $h_A$ may be greater than 5 times the width $w_A$.

Figure 5:
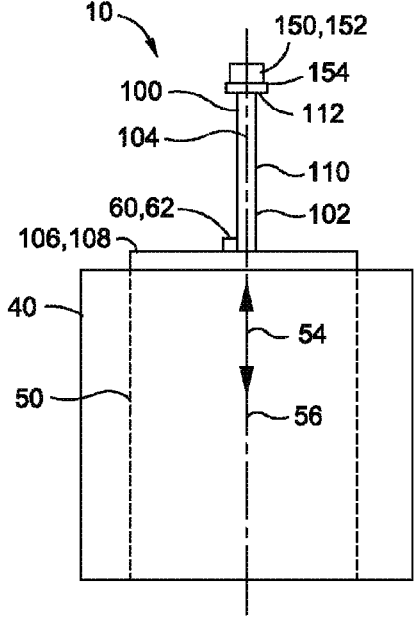
FIG. 5 is side view illustration of the system taken along line 5-5 of FIG. 3 and illustrating a height of the axial beam being greater than a width of the axial beam.

FIG. 5 is a further side view of the axial beam 110 mounted to the shaker 40 armature 50 and illustrating the test article 150 mounted to the holding fixture 154 which is mounted to the free end of the axial beam 110. The long axis 104 of the resonance beam 102 is shown aligned with the reference axis 56 of the shaker 40 such that the reference axis 56 passes through the axial beam 110. In such an arrangement, the shock pulse 54 may be imparted to the axial beam 110 without eccentrically loading the axial beam 110. However, the axial beam 110 may be offset (not shown) from the reference axis 56 which may alter the excitation of the axial beam 110 and which may result in different levels of magnification in the axial beam 110.

Referring to FIGS. 6-9, shown is an embodiment of the system 10 wherein the resonance beam 102 is configured as a transverse beam 120 having a long axis 104 oriented substantially perpendicular to the reference axis 56. The transverse beam 120 may have a base portion 106 which may comprise the portion where the transverse beam 120 interfaces with or is mounted to the armature 50. In an embodiment, the base portion 106 of the transverse beam 120 may comprise an adapter plate 108 similar to the adapter plate 108 that may be included with the axial beam 110 discussed above.

The transverse beam 120 has opposing beam ends 122. The long axis 104 extends between the beam ends 122. The test article 150 is shown mounted to one of the beam ends 122. However, the test article 150 may be mounted at any location between the beam ends 122 and on any surface of the transverse beam 120. At least one accelerometer 62 may be mounted to the transverse beam 120 to measure the acceleration response of the transverse beam 120 at the location. For example, an accelerometer 62 may be mounted to the transverse beam 120 at a location proximate the test article 150. Another accelerometer 62 may be mounted to the transverse beam 120 at the location of the base portion 106 to measure acceleration response at the base portion 106 for comparison to the acceleration response at another location on the transverse beam 120.

Figures 6, 7:
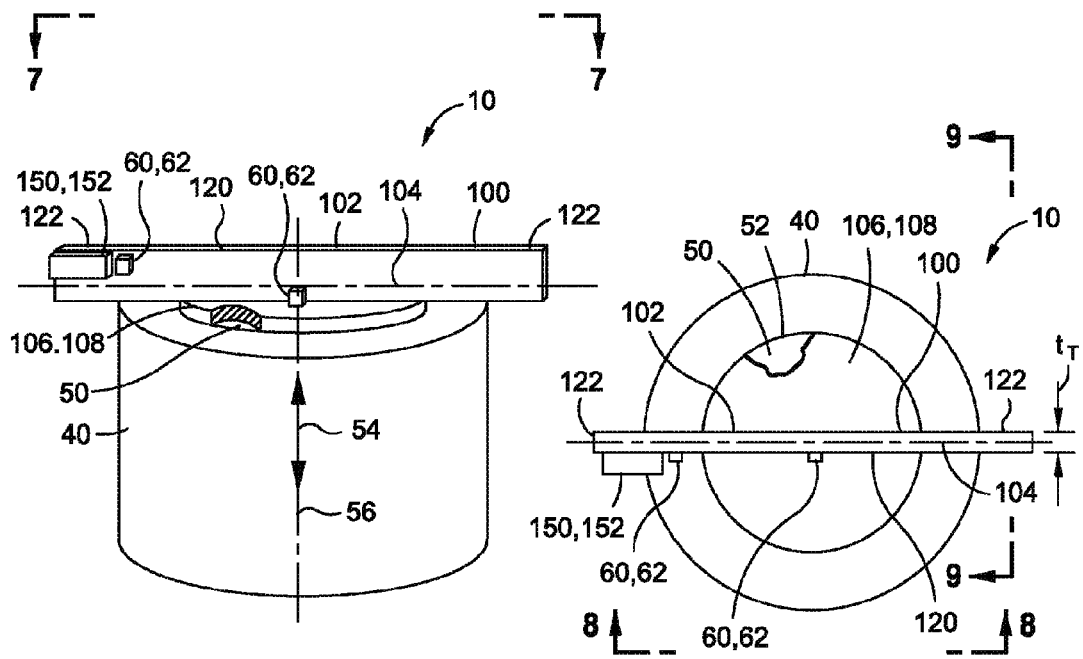
FIG. 6 is a perspective illustration of an embodiment of the system wherein the resonance beam is configured as a transverse beam.
FIG. 7 is top view illustration of the system taken along line 7-7 of FIG. 6 and illustrating the transverse beam mounted to the shaker.

FIG. 7 is a top view of the system showing the transverse beam 120 generally centered on the shaker 40. The transverse beam 120 may have a thickness $t_T$ which may be less than a height $h_T$ of the transverse beam 120. In an embodiment, the thickness $t_T$ may be no greater than approximately one-half a height $h_T$ (FIG. 8) of the transverse beam 120 although the transverse beam 120 may be provided in any thickness $t_T$.

Figures 8, 9:
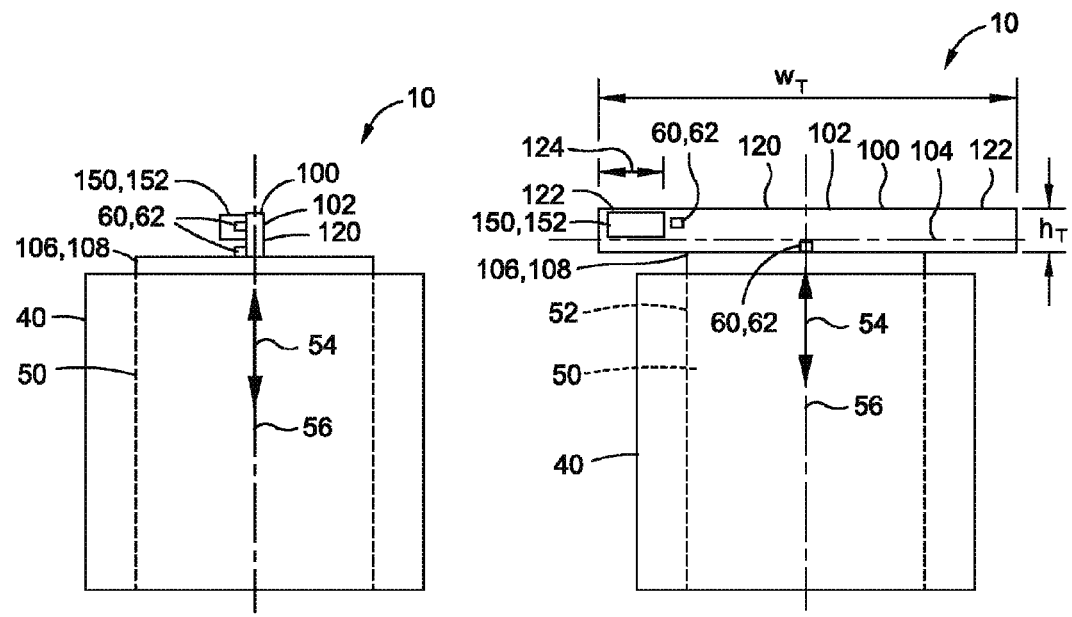
FIG. 8 is side view illustration of the system taken along line 8-8 of FIG. 7 and illustrating the shock pulse imparted to the transverse beam.
FIG. 9 is side view illustration of the system taken along line 9-9 of FIG. 7 and illustrating a width of the transverse beam being greater than a height of the transverse beam.

FIG. 8 is a side view of the transverse beam 120 mounted to the shaker 40. The transverse beam 120 may have a height $h_T$ measured perpendicular to the long axis 104 and a width $w_T$ measured parallel the long axis 104. In an embodiment, the width $w_T$ may be greater than the height $h_T$. For example, the width $w_T$ of the transverse beam 120 may be at least twice the height $h_T$ of the transverse beam 120. In a further embodiment, the width $w_T$ of the transverse beam 120 may be 2 to 10 times greater than the height $h_T$ of the transverse beam 120 although longer widths $w_T$ are contemplated.

The width $w_T$ of the transverse beam 120 may be such that at least one of the beam ends 122 extends beyond a perimeter 52 of the armature 50. The difference between the beam end 122 and the armature 50 perimeter 52 may define an overhang 124 of the transverse beam 120 wherein the beam end 122 is cantilevered outwardly from the armature 50. In such an arrangement, the transverse beam 120 may be excited into a flexural mode of resonance at least in the overhang 124 area. In this regard, the beam end 122 may comprise an anti-node (not shown) of the excitation and may exhibit increased magnification of the shock pulse 54 at the beam end 122 relative to the magnification at other locations of the transverse beam 120.

FIG. 9 is a further side view of the transverse beam 120 illustrating the generally rectangular cross sectional shape of the transverse beam 120. However, the transverse beam 120 may be provided in an alternative cross sectional shape including a square cross sectional shape or other cross sectional shapes. FIG. 9 further illustrates the transverse beam 120 mounted such that the reference axis 56 passes through the transverse beam 120. However, the transverse beam 120 may be offset from the reference axis 56 which may alter the excitation and magnification level at one or more locations of the transverse beam 120. The test article 150 and accelerometer 62 are shown mounted on a side surface of the transverse beam 120. However, the test article 150 and accelerometer 62 may be mounted on other surfaces of the transverse beam 120 such that the test article 150 may be shock tested along different axes. For example, after shock testing the test article 150 mounted to the side surface at the beam end 122, the test article 150 may be mounted to the top surface of the transverse beam 120 at the beam end 122 and another shock pulse 54 may be applied to the transverse beam 120.

Referring to FIGS. 10-13, shown is an embodiment of the system 10 wherein the resonance beam 102 is configured as an L-beam 130 having an axial beam 110 and a lateral element 132 mounted to the axial beam 110. The axial beam 110 may be configured in a manner similar to the axial beam 110 shown in FIGS. 2-5. The axial beam 110 may be mounted such that the long axis 104 is oriented substantially parallel to the reference axis 56 of the shaker 40. In the embodiment shown, the shaker 40 may be pivoted such that the reference axis 56 is oriented approximately horizontally instead of the reference axis 56 being vertically oriented as shown in FIGS. 2-5. In the horizontal orientation, at least a portion of the axial beam 110 may be supported on a beam support 138 which may comprise a non-movable object preferably of high mass and rigidity. For example, the beam support 138 may be configured as a granite table. A layer 140 of low-friction fluid may optionally included between the axial beam 110 and the beam support 138 to facilitate slidable movement of the axial beam 110 during application of the shock pulse 54. For example, the low-friction fluid may comprise hydraulic fluid although any low-friction fluid may be used.

The lateral element 132 extends outwardly from the axial beam 110 and may have a fixed end 134 and a free end 136. The fixed end 134 may be mounted to the axial beam 110. The test article 150 may be mounted to the free end 136 or at any other location between the free end 136 and the fixed end 134. The lateral element 132 may extend outwardly from the axial beam 110 and may be oriented substantially perpendicularly relative to the axial beam 110. However, the lateral element 132 may be oriented non-perpendicularly relative to the axial beam 110. The test article 150 may be mounted to the lateral element 132 on any one of the side surfaces thereof. An accelerometer 62 may likewise be mounted to the lateral element 132 proximate the test article 150 to measure acceleration during application of the shock pulse 54 for comparison to acceleration measured at the base portion 106 to determine the magnification level.

FIG. 11 is a top view of the L-beam 130 mounted to the shaker 40. The lateral element 132 may be mounted adjacent the free end 136 of the axial beam 110 or at other locations on the axial beam 110. In addition, although the lateral element 132 is shown as being generally centered relative to the reference axis 56, the lateral element 132 may be offset from the reference axis 56 which may alter the magnification of the lateral element 132. The test article 150 is shown mounted to one of the sides of the square tube lateral element 132. However, as indicated above, the test article 150 may be mounted to a different one of the sides to provide a different magnification and response in the test article 150.

The lateral element 132 is shown configured as a square tube. Advantageously, the square tube shape may facilitate mounting the test article 150 in different mutually orthogonal orientations as may be required for testing the test article in each of three mutually perpendicular axes. In an embodiment, the square tube may have a wall thickness $t_{wall}$ and a width $w_T$ of approximately 4×4 inches although the lateral element 132 may be provided in any wall thickness $t_{wall}$ and a width $w_T$. In addition, the lateral element 132 may be provided in alternative cross sectional shapes, sizes and configurations to achieve a desired magnification level. For example, the lateral element 132 may be configured as a generally hollow rectangular tube, as a hollow cylindrical tube, or in any other hollow or solid cross sectional configurations. The lateral element 132 may be sized and configured such that at least one location on the lateral element 132 has a measured peak acceleration 206 that is greater than the measured peak acceleration 206 at the base portion 106. An accelerometer 62 may be mounted at the base portion and on the lateral element 132 at a location proximate the test article 150 to measure acceleration during the shock pulse 54.

FIG. 12 is a side view of the shaker 40 oriented such that the reference axis 56 is substantially horizontal. The mass of the L-beam 130 is supported by the beam support 138 (e.g., a granite table) having the optional layer 140 of low-friction fluid at the interface between the axial beam 110 and the beam support 138. The lateral element 132 has a height $h_L$ which may be selected to provide a desired amount of displacement at a free end 136 of the lateral element 132 during the shock pulse 54. The shock pulse 54 imparted to the L-beam 130 may cause the axial beam 110 to move relative to the beam support 138. The L-beam 130 may be excited into one or more resonant modes including a longitudinal mode of excitation in the axial beam 110 and a flexural mode of excitation in the lateral element 132 and resulting in increased magnification of the shock output at the lateral element 132.

FIG. 13 is a front view of the system 10 illustrating the lateral element 132 generally centered relative to the reference axis 56 (FIG. 12) of the shaker 40. However, as indicated above, the lateral element 132 may be offset from the reference axis 56 of the shaker 40. Offsetting the lateral element 132 may alter the magnification of the shock pulse in the lateral element 132.

In the embodiments illustrated in FIGS. 1-13 and described above, the resonance beam 102 is preferably configured such that at least one location on the resonance beam 102 has a measured peak acceleration 206 that is greater than the measured peak acceleration 206 at the base portion 106. For example, the resonance beam 102 is preferably configured such that at least one location proximate the free end 136 of the resonance beam 102 has a measured peak acceleration 206 that is at least twice the measured peak acceleration 206 at the base portion 106. Measurements of the peak acceleration on the resonance beam 102 may be provided by one or more of the acceleration sensors 60 or accelerometers 62. For example, at least one accelerometer 62 may be mounted at the base portion 106 of the resonance beam 102. Another accelerometer 62 may be mounted proximate the article under test 150. The acceleration at the free end 136 may be compared to the measured acceleration at the base portion 106 to determine the magnification level provided by the resonance beam 102.

The identification of the locations of magnified acceleration may be performed with a mass model 152 of the article under test 150. The mass model 152 may be mounted at different locations where the acceleration response is to be measured. The mass model 152 may simulate the total mass of the article under test 150 and its mass distribution. The mass model 152 may provide a means for more accurately identifying the accelerations levels at different locations on the resonance beam 102 without the risk of damaging delicate and/or expensive actual test articles 150. Such risk of damage may occur in an over-test condition where an excessively high magnitude shock pulse 54 may be applied to the resonance beam 102. After identifying one or more locations on the resonance beam 102 having a desired magnification level, the mass model 152 may be removed from the resonance beam 102 and replaced with the actual component to be tested (i.e., the article under test). The article under test 150 may be subjected to one or more shock pulses 54 and assessed for indications of malfunction or damage.

For any one of the embodiments illustrated in FIGS. 1-13, the resonance beam 102 (FIG. 1) may be configured such that at least one location exhibits a simulated SRS 218 (FIG. 15) that is substantially equivalent to the desired SRS 208 (FIG. 15). As indicated above, the simulated SRS 218 may be calculated based on the measured acceleration at a given location on the resonance beam 102. In an embodiment, the resonance beam 102 may be configured such that the simulated SRS 218 is within a specified tolerance band 214 (FIG. 15) of the desired SRS 208. For example, the resonance beam 102 may be configured such that the absolute peak acceleration 224 (FIG. 15) of the simulated SRS 218 is within a tolerance band 214 of approximately +/−6 dB of the acceleration at the knee frequency 216 (FIG. 15) of the desired SRS 208. The knee frequency 216 may be defined as the location on an SRS plot where the slope of the SRS curve changes to a constant or slightly decreasing acceleration value. In terms of the structure or the service environment that the SRS represents, the knee frequency 216 may be defined as the dominant frequency of the pyrotechnic shock environment at the measured location. The desired SRS 208 may be provided with a tolerance band 214 that varies with the frequency of the desired SRS 208. For example, the desired SRS 208 may be provided with a tolerance band 214 of +/−3 dB for frequencies that are less than approximately 3 kHz and +9/−6 dB for frequencies greater than 3 kHz. Other tolerance band variations are contemplated.

In an embodiment, the resonance beam 102 (FIG. 1) may be configured such that at least one location on the resonance beam 102 exhibits a simulated SRS 218 (FIG. 15) having an absolute peak acceleration 224 (FIG. 15) of greater than approximately 5000 g's. In a further embodiment, the simulated SRS 218 may have an absolute peak acceleration 224 of greater than approximately 20,000 g's or more. Furthermore, the resonance beam 102 may be configured such that the simulated SRS 218 includes acceleration data of up to approximately 100 kHz or greater. Advantageously, the combination of the shaker 40 (FIG. 1) and resonance beam 102 (FIG. 1) may provide acceleration response that accurately simulates the high-frequency, high-magnitude transient shock of a pyrotechnic event.

In this regard, the combination of the resonance beam 102 (FIG. 1) and shaker 40 (FIG. 1) may be configured to simulate at least one of three environmental categories of pyrotechnic shock including a far-field environment, a mid-field environment, and a near-field environment. For simulating a far-field environment, the resonance beam 102 may advantageously be sized and configured to magnify the shock pulse 54 (FIG. 1) such that for at least one location on the resonance beam 102, the resonance beam 102 exhibits a simulated SRS 218 (FIG. 15) having an absolute peak acceleration 224 (FIG. 15) of up to approximately 1000 g's. For the simulated SRS 218 of a far-field environment, the spectrum may include acceleration data of up to 10 kHz. In an embodiment of the resonance beam 102 that may be suited for simulating a far-field environment, the axial beam 110 (FIGS. 2-5) may be appropriate for producing lower intensity (i.e., magnitude) response relative to the response produced by the transverse beam 120 (FIGS. 6-9) or L-beam 130 (FIGS. 10-13) embodiments. Advantageously, due to the inherently higher stiffness or rigidity of the axial beam 110 relative to the stiffness of the transverse beam 120 or L-beam 130 embodiments, the simulated SRS 218 of the axial beam 110 embodiment may provide a more controlled response to the shock pulse 54. In this regard, the simulated SRS 218 of the axial beam 110 may have a smoother curve that may closely follow the straight-line approximation of the desired SRS 208 with minimal peaks and valleys in the simulated SRS 218.

For simulating a mid-field environment, the resonance beam 102 (FIG. 1) may be sized and configured to magnify the shock pulse 54 (FIG. 1) such that for at least one location on the resonance beam 102, the resonance beam 102 exhibits a simulated SRS 218 (FIG. 15) having an absolute peak acceleration 224 (FIG. 15) of between approximately 1000 g's and 5000 g's. For the simulated SRS 218 of a mid-field environment, the spectrum may also contain acceleration data greater than approximately 10 kHz. In an embodiment for simulating a mid-field environment of pyrotechnic shock, the transverse beam 120 (FIGS. 6-9) embodiment of the resonance beam 102 may be well-suited.

For simulating a near-field environment, the resonance beam 102 (FIG. 1) may be sized and configured to magnify the shock pulse 54 (FIG. 1) such that for at least one location on the resonance beam 102, the resonance beam 102 exhibits a simulated SRS 218 (FIG. 15) having an absolute peak acceleration 224 (FIG. 15) of greater than approximately 5000 g's. In addition, the simulated SRS 218 of a near-field environment may include spectral content above approximately 100 kHz. In an embodiment for simulating a near-field environment, the L-beam 130 (FIGS. 10-13) embodiment of the resonance beam 102 may advantageously produce a higher intensity (i.e., higher magnitude) response than the response produced by the axial beam 110 or the transverse beam 120. In addition, the spectral content of the simulated SRS 218 of the L-beam 130 may include greater variation (i.e., more peaks and valleys). A portion of the spectrum may fall outside of a given tolerance band 214.

In any of the embodiments illustrated in FIGS. 1-13, the resonance beam 102 (FIG. 1) may be formed of a material that produces the desired magnification. The material of the resonance beam 102 may be selected based upon the mechanical properties such as the stiffness or modulus of elasticity and/or Poisson's ratio as such properties may affect the excitation of the resonance beam 102. In an embodiment, the resonance beam 102 may be formed of magnesium due to its comparable strength properties and low density relative to other high performance metals such as aluminum. In this regard, a resonance beam 102 formed of magnesium may be provided in a larger physical size (e.g., thicker) than an aluminum resonance beam 102 of the same mass such that the magnesium resonance beam 102 may have a higher stiffness. Advantageously, the higher stiffness of magnesium may minimize attenuation of high frequency shock when compared to an aluminum resonance beam 102 of the same dimensions. The resonance beam 102 may be formed in any one of a variety of materials including, but not limited to, magnesium, aluminum, steel, titanium, graphite epoxy composite and any other metallic or non-metallic material or combination thereof.

Figure 14:
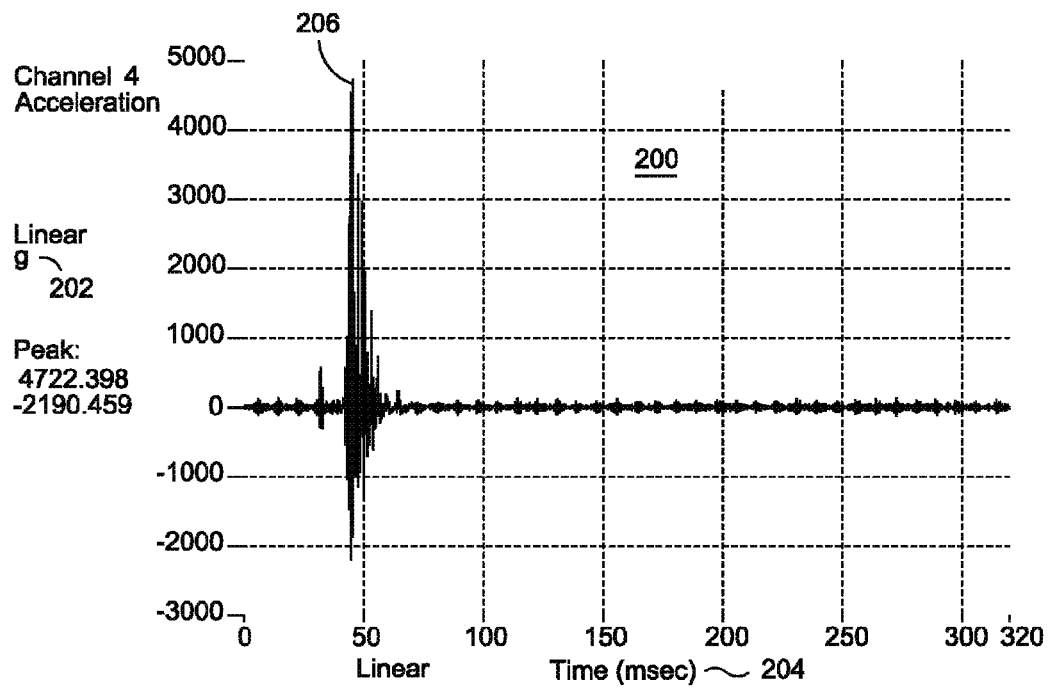
FIG. 14 is a plot of the acceleration time history of an axial beam in response to a first shock pulse for an arrangement similar to that which is illustrated in FIGS. 2-5.

FIG. 14 is a plot of acceleration 202 (g's) vs. time 204 (milliseconds) for the acceleration time history 200 of a presently disclosed embodiment of the axial beam 110 (FIGS. 2-5) subjected to a shock pulse 54 (FIG. 1). The axial beam 110 was configured similar to the configuration shown in FIGS. 2-5. The acceleration time history 200 in FIG. 14 shows a measured peak acceleration 206 of approximately 4722 g's as a result of a shock pulse 54 from the shaker 40.

FIG. 15 is a simulated SRS 218 based on the acceleration time history 200 of FIG. 14. The simulated SRS 218 is superimposed over a desired SRS 208 which has a damping ratio 212 of 5 percent and a tolerance band 214 with upper and lower limits 214a, 214b. The simulated SRS 218 has an absolute peak acceleration 224 that is calculated based on the measured peak acceleration 206 of FIG. 14. In FIG. 15, the absolute peak acceleration 224 is approximately 8970 g's. As can be seen, the simulated SRS 218 substantially simulates the desired SRS 208. In this regard, the simulated SRS 218 is tightly controlled as evidenced by the simulated SRS 218 being maintained within the tolerance band 214 of the desired SRS 208. Furthermore, the absolute peak acceleration 224 in FIG. 15 advantageously occurs approximately at the knee frequency 216 of the desired SRS 208. In this regard, the simulated SRS 218 illustrates that the first mode of vibration of the axial beam 110 advantageously has a frequency that is substantially similar to the knee frequency 216 of the desired SRS 208.

Figure 16:
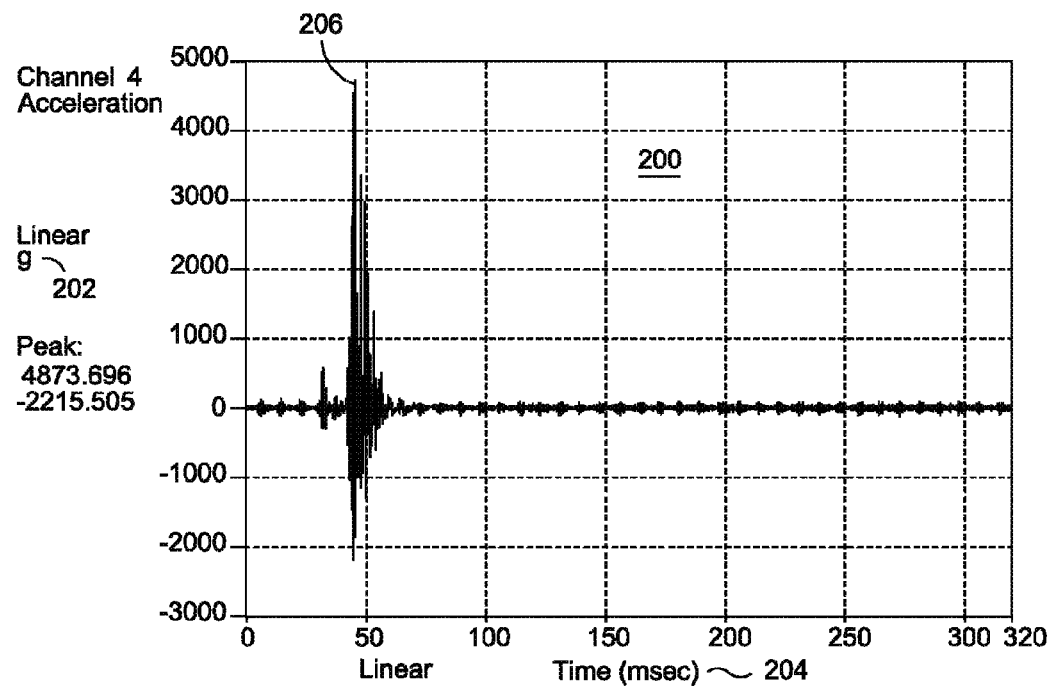
FIG. 16 is a plot of the acceleration time history of the axial beam subject to a second shock pulse similar to the first shock pulse illustrated in the plots of FIGS. 14-15.

FIG. 16 is plot of the acceleration time history 200 of the axial beam 110 (FIGS. 2-5) subjected to the same shock pulse 54 (FIG. 1) using the same shaker 40 (FIG. 1) and axial beam 110 configuration represented in the plots of FIG. 14. As can be seen, the acceleration time history 200 of FIG. 16 is substantially similar to the acceleration time history 200 illustrated in FIG. 14. For example, the acceleration time history 200 in FIG. 16 has a measured peak acceleration 206 of approximately 4870 g's which closely corresponds to the measured peak acceleration 206 of approximately 4722 g's of FIG. 14. In this regard, FIGS. 14 and 16 illustrate the control and repeatability of the shock pulse 54 and the acceleration response provided by the shaker 40/resonance beam 102 arrangement of the present disclosure.

Figure 17:
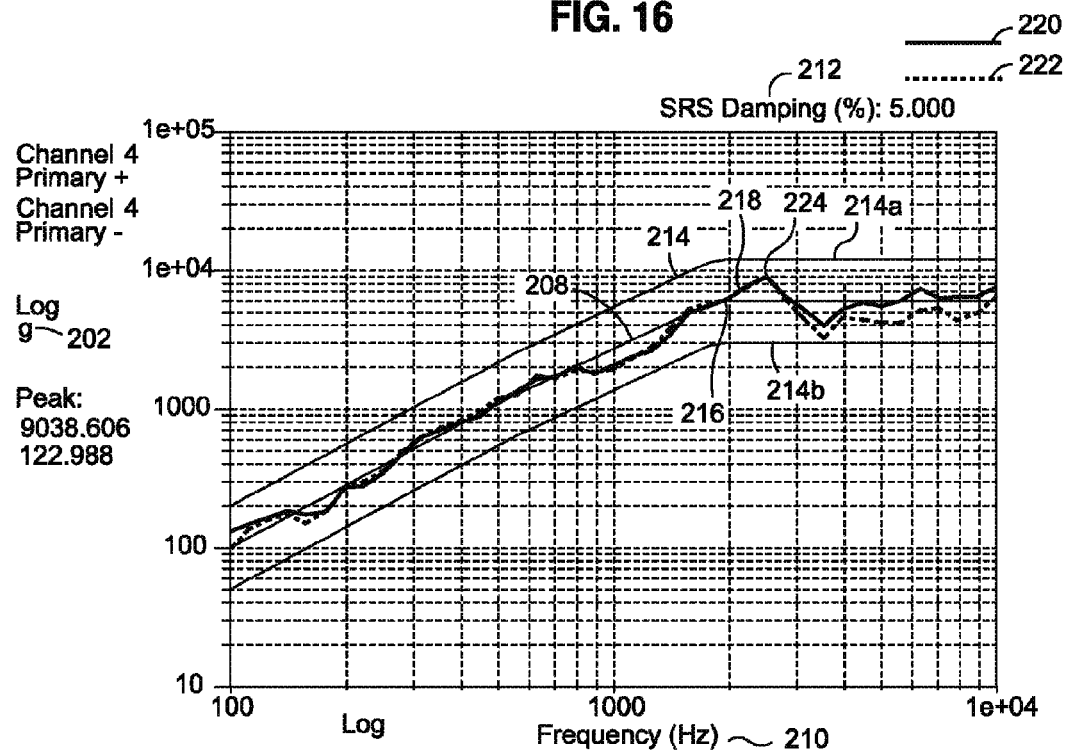
FIG. 17 is a simulated SRS associated with the second shock pulse and based on the acceleration time history of FIG. 16 and illustrating the close correspondence with the simulated SRS associated with the first shock pulse illustrated in FIG. 15.

FIG. 17 is a simulated SRS 218 based on the acceleration time history 200 of FIG. 16. The simulated SRS 218 of FIG. 16 is superimposed over the desired SRS 208 and illustrates the relatively tight control of the shock pulse 54 (FIG. 1) as evidenced by the simulated SRS 218 closely approximating the desired SRS 208. For example, the absolute peak acceleration 224 of approximately 9040 g's in FIG. 17 closely corresponds to the absolute peak acceleration 224 of approximately 8970 g's in FIG. 15 and illustrates the precise control and repeatability of the shock pulse 54 using the shaker 40/resonance beam 102 (FIG. 1) combination.

Figure 18:
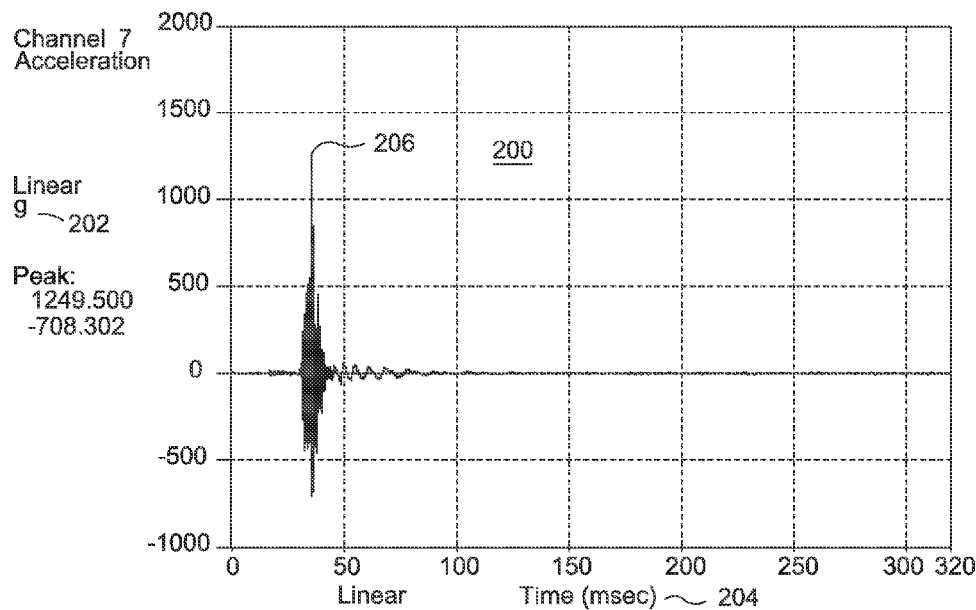
FIG. 18 is a plot of the acceleration time history measured at a base portion of the axial beam of FIGS. 2-5 and having a measured peak acceleration at the base portion of approximately 1250 g's.

FIG. 18 is a plot of the acceleration time history 200 of the axial beam 110 (FIGS. 2-5) measured at a base portion 106 (FIGS. 2-5) thereof. As illustrated in FIGS. 2-5, the base portion 106 of the axial beam 110 may comprise the location where the axial beam 110 interfaces with or is mounted to the armature 50. The acceleration response at the base portion 106 may be measured with an accelerometer 62 as shown in FIGS. 2 and 4-5. In FIG. 18, the base portion 106 has a measured peak acceleration 206 of approximately 1250 g's.

Figure 19:
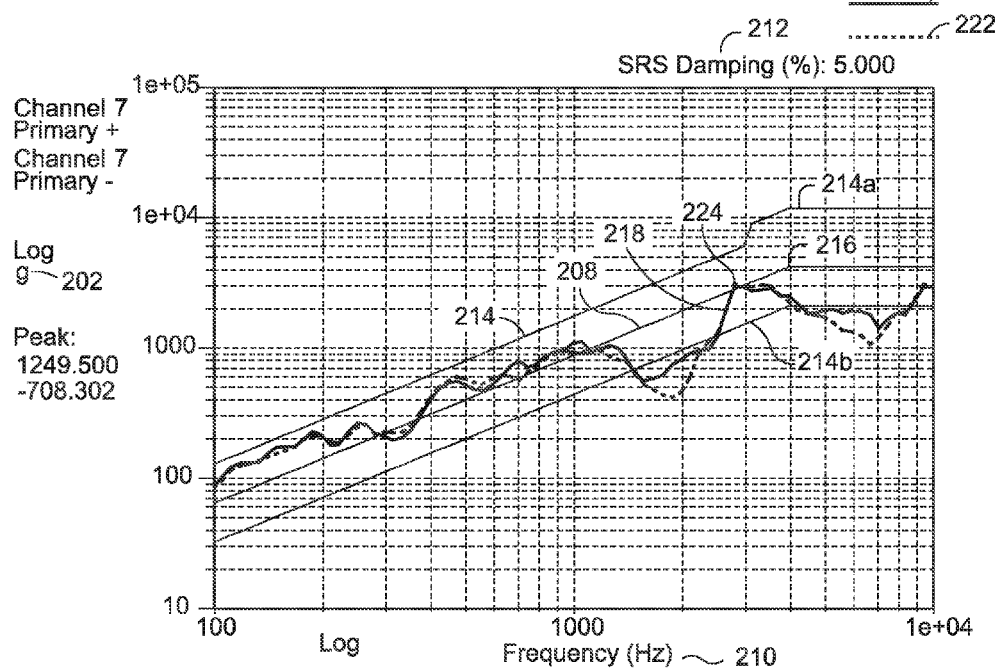
FIG. 19 is a simulated SRS based on the acceleration time history of FIG. 18 and illustrating an absolute peak acceleration at the base portion of approximately 2951 g's.

FIG. 19 is a simulated SRS 218 based on the acceleration time history 200 of the base portion 106 as shown in FIG. 18. The simulated SRS 218 has an absolute peak acceleration 224 of approximately 2951 g's at the base portion 106.

Figure 20:
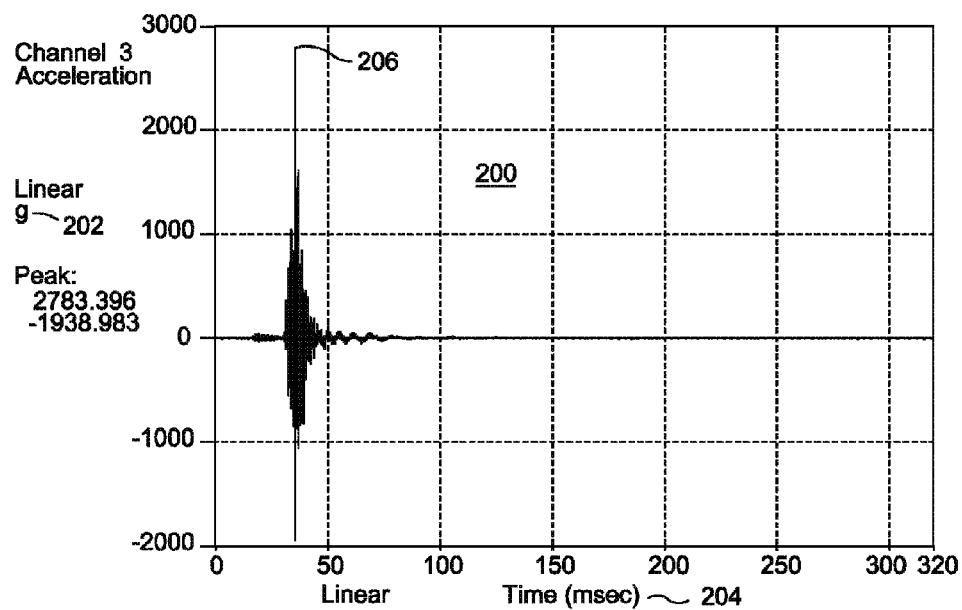
FIG. 20 is a plot of the acceleration time history measured at a free end of the axial beam of FIGS. 2-5 and having a measured peak acceleration at the free end of approximately 2784 g's.

FIG. 20 is a plot of the acceleration time history 200 of the axial beam 110 (FIGS. 2-5) measured at a free end 136 (FIGS. 2-5) thereof. The free end 136 of the axial beam 110 is located opposite the base portion 106 (FIGS. 2-5). The acceleration response at the free end 136 may be measured with an accelerometer 62 (FIG. 2). In FIG. 20, the free end 136 has a measured peak acceleration 206 of approximately 2784 g's which is a magnification of more than twice the measured peak acceleration 206 of approximately 1250 g's at the base portion 106 of the axial beam 110.

Figure 21:
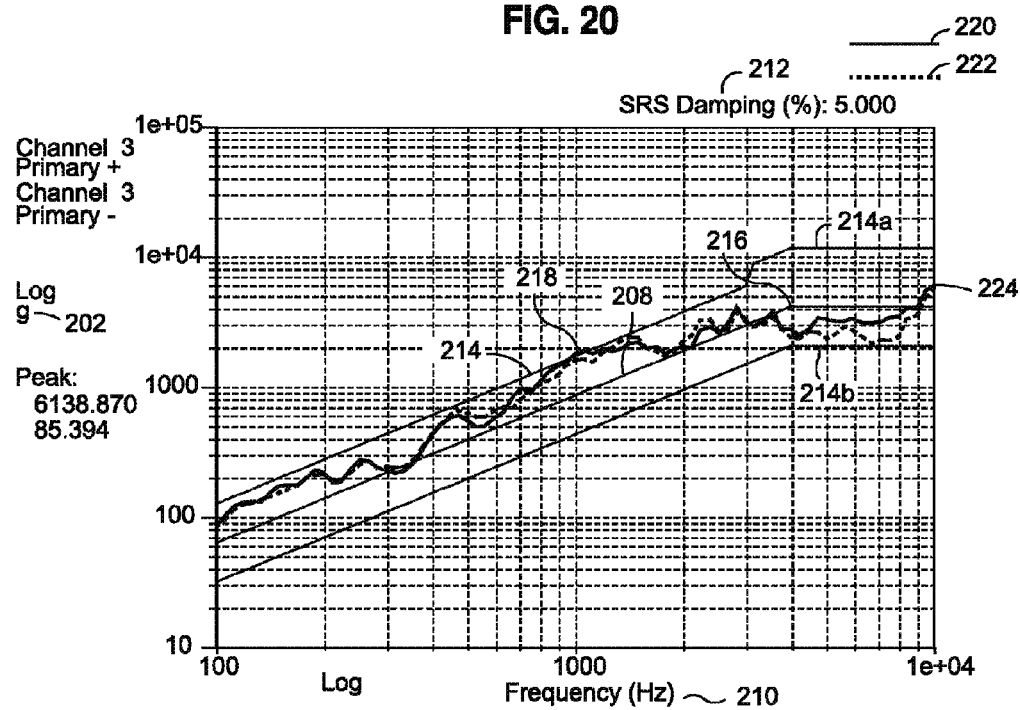
FIG. 21 is a simulated SRS based on the acceleration time history of FIG. 20 and illustrating an absolute peak acceleration at the free end of approximately 6139 g's.

FIG. 21 is a simulated SRS 218 based on the acceleration time history 200 shown in FIG. 19. The simulated SRS 218 has an absolute peak acceleration 224 of approximately 6140 g's as compared to the absolute peak acceleration 224 of approximately 2951 g's at the base portion 106 of the axial beam 110 (FIGS. 2-5) and further illustrating the magnification capability of the axial beam 110. FIG. 21 further illustrates the relatively tight control of the shock pulse 54 (FIGS. 2-5) as evidence by the simulated SRS 218 being generally maintained within the tolerance band 214 of the desired SRS 208 with the exception of a relatively narrow-band exceedance at approximately 1000 Hz. Such exceedances within a relatively narrow band may generally be acceptable when it is determined that the accelerations at such frequencies pose a minor threat to an article under test. Furthermore, the mounting location of the article under test 150 on the axial beam 110 may be adjusted to bring the simulated SRS 218 within the tolerance band 14. In addition, the transient signal waveform may be electronically adjusted such as by adjusting the analog filter 16 (FIG. 1) and/or the digital filter 18 (FIG. 1) to alter the magnitude of the transient signal at one or more frequencies to bring a substantial majority of the spectrum of the simulated SRS 218 to within the tolerance band 14.

Figure 22:
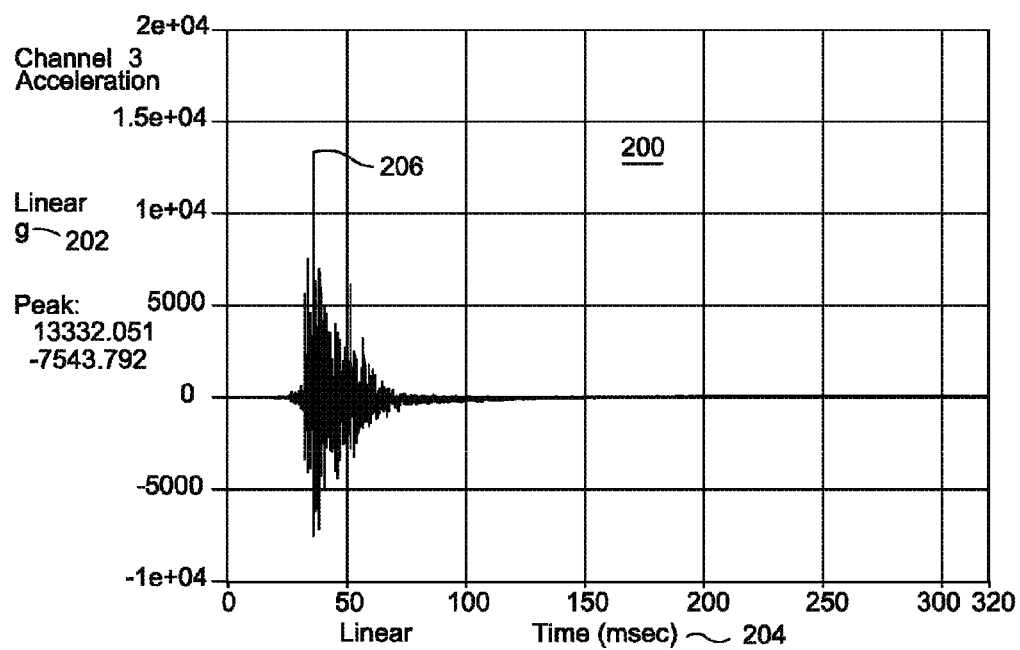
FIG. 22 is a plot of an acceleration time history of an L-beam embodiment similar to that which is illustrated in FIGS. 10-13 and having a measured peak acceleration of approximately 13,332 g's.

FIG. 22 is a plot of the acceleration time history 200 of an L-beam 130 (FIGS. 10-13) embodiment of the resonance beam 102 (FIG. 1) similar to that which is illustrated in FIGS. 10-13. The acceleration time history 200 may be measured at a location on the lateral element 132 (FIGS. 10-13) of the L-beam 130 such as with an accelerometer 62 (FIGS. 10-13). In FIG. 22, the L-beam 130 has a measured peak acceleration 206 of approximately 13,330 g's which corresponds to a level of shock attained using explosive materials.

Figure 23:
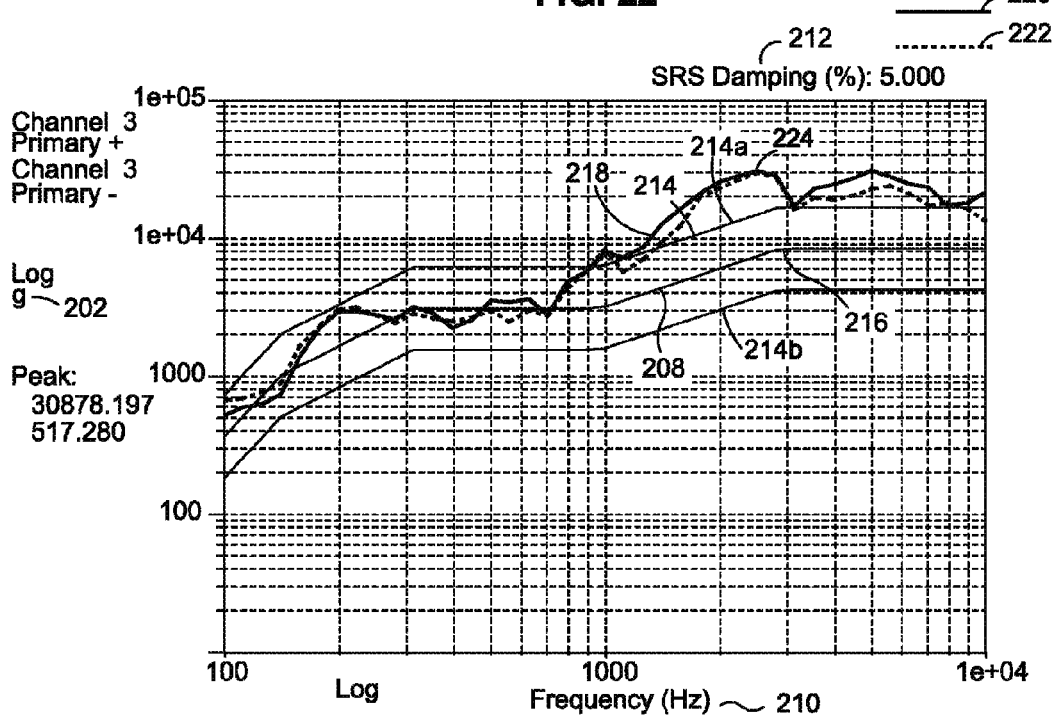
FIG. 23 is a simulated SRS based on the acceleration time history of FIG. 22 and illustrating an absolute peak acceleration of the L-beam of approximately 30,880 g's.

FIG. 23 is a simulated SRS 218 based on the acceleration time history 200 of the L-beam 130 (FIGS. 10-13) plotted in FIG. 22. The simulated SRS 218 has an absolute peak acceleration 224 of approximately 30,880 g's which is also comparable to the level of shock produced by explosives. In this regard, FIG. 23 is presented to illustrate the capability of the resonance beam 102 (FIG. 1) to simulate high-intensity pyrotechnic shock. It should also be noted that FIG. 23 represents the magnification capability of the L-beam 130 (FIGS. 10-13) test fixture prior to adjustment of the L-beam 130 or the electronic test equipment to bring the simulated SRS 218 within the tolerance band 14 for the entire spectrum. In this regard, the physical location of the article under test 150 on the L-beam 130 (FIGS. 10-13) may be adjusted or the transient signal waveform may be adjusted to bring a substantial portion of the spectrum or the entire spectrum of the simulated SRS 218 to within the tolerance band 14.

Figure 24:
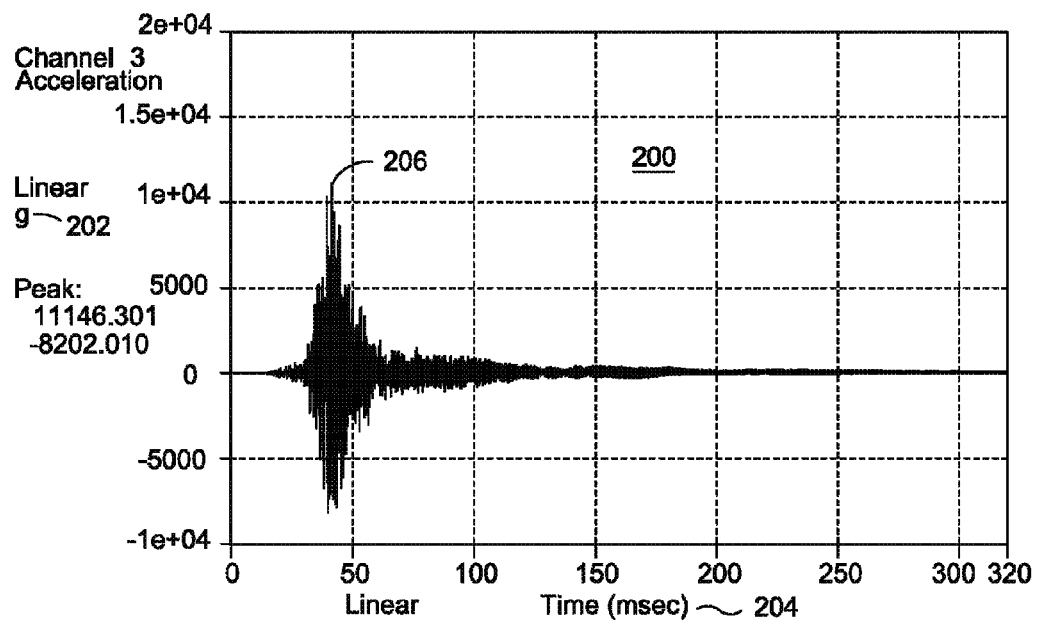
FIG. 24 is a plot of an acceleration time history of an L-beam embodiment similar to that which is illustrated in FIGS. 10-13 and having a measured peak acceleration of approximately 11,146 g's.

FIG. 24 is an additional plot of an acceleration time history 200 of an L-beam 130 (FIGS. 10-13) embodiment configured similar to the L-beam 130 shown in FIGS. 10-13. The acceleration time history 200 has a measured peak acceleration 206 of approximately 11,146 g's measured on the lateral element 132 of the L-beam 130.

Figure 25:
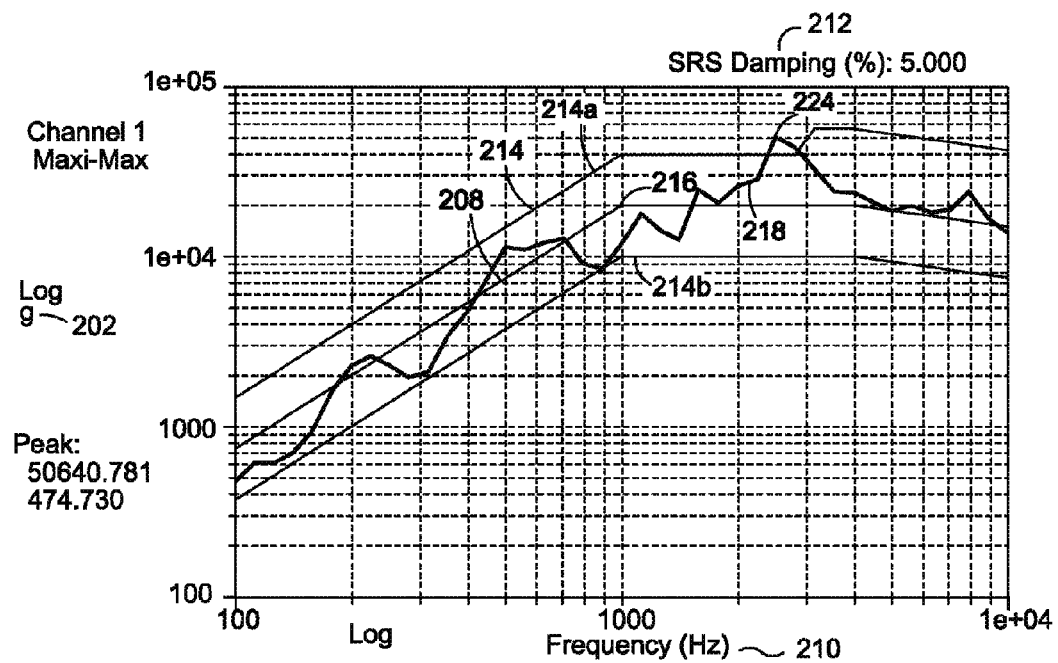
FIG. 25 is a simulated SRS based on the acceleration time history of FIG. 24 and illustrating an absolute peak acceleration of the L-beam of approximately 50,641 g's.

FIG. 25 is a simulated SRS 218 based on the acceleration time history 200 of FIG. 24. The simulated SRS 218 has an absolute peak acceleration 224 of approximately 50,641 g's further illustrating the capability of the resonance beam 102 (FIG. 1) to generate high-intensity shock. FIG. 25 also illustrates the generally tight control of the shock pulse 54 as evidenced by the simulated SRS 218 being generally maintained within the tolerance band 214 of the desired SRS 208 with minor exceedances within a relatively narrow-band. In this regard, it should be noted that FIG. 25 illustrates the magnification capability of the L-beam 130 (FIGS. 10-13) test fixture prior to adjustment of the L-beam 130 test setup to bring minor exceedances of the simulated SRS 218 within the tolerance band 14.

Figure 26:
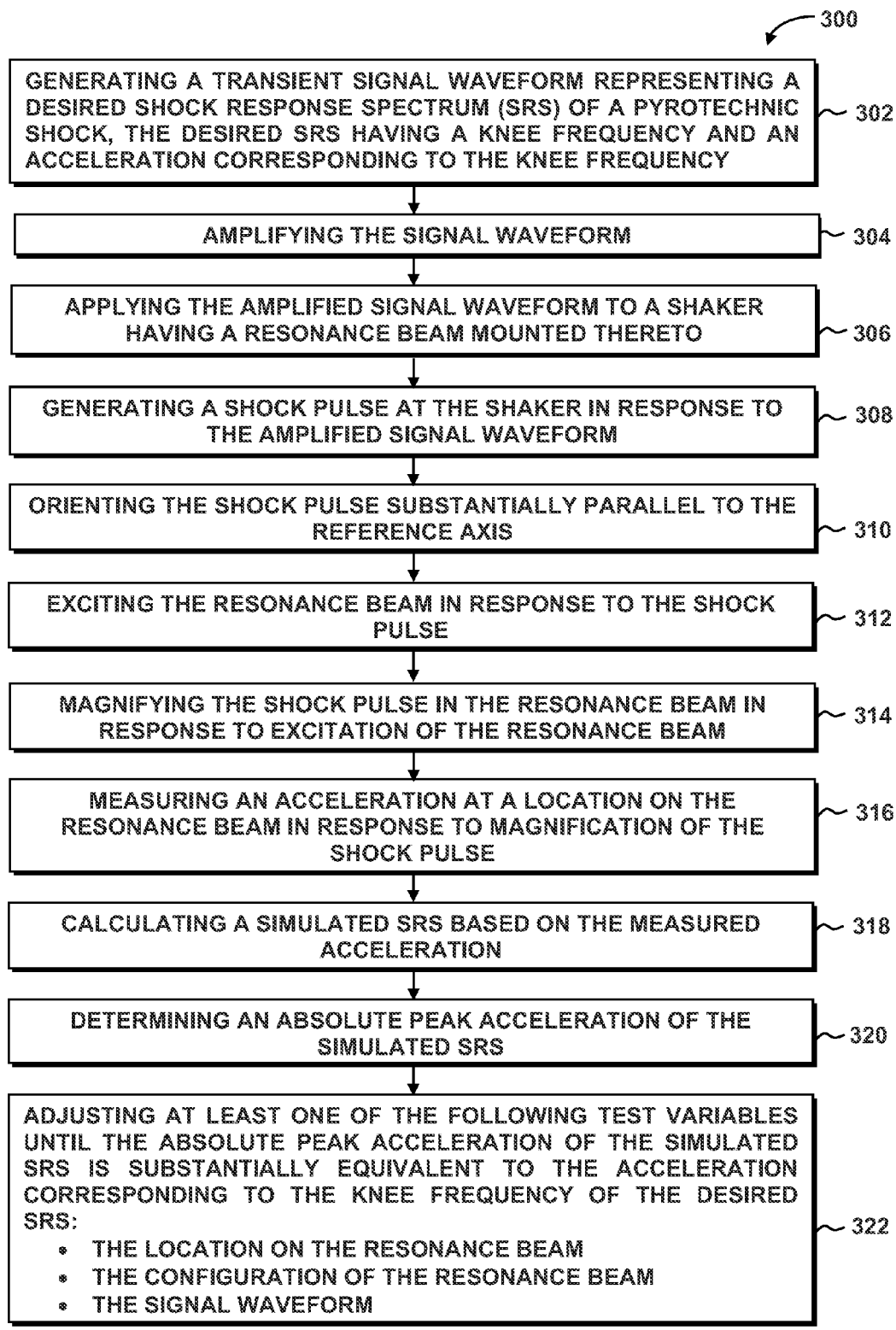
FIG. 26 is a flow chart illustrating an embodiment of a methodology including one or more operations that may be implemented in a system for simulating pyrotechnic shock in a test article.

FIG. 26 is a flow chart illustrating an embodiment of a methodology 300 including one or more operations that may be implemented in a system 10 (FIG. 1) for simulating pyrotechnic shock. The methodology may comprise step 302 of generating a transient signal waveform representing the desired SRS 208. The transient signal waveform may be generated by the pulse signal generator 12 (FIG. 1) and may have a desired magnitude (i.e., voltage) and duration (i.e., ms) for achieving a desired profile in the shock pulse 54 (FIG. 1) generated by the shaker 40 (FIG. 1).

Step 304 of the methodology 300 may comprise amplifying the signal waveform such as by using the electrical power amplifier 28 (FIG. 1). The power amplifier 28 may initially provide direct current to the field coil 48 (FIG. 1) of the shaker 40 (FIG. 1) to generate a magnetic field surrounding the armature 50 (FIG. 1). The power amplifier 28 may also amplify the transient signal waveform and generate alternating current representing the transient signal waveform to the armature 50.

Step 306 may comprise applying the amplified signal waveform to the electrodynamic shaker 40 (FIG. 1). The amplified signal waveform energizes the armature 50 (FIG. 1) and causes the armature 50 to move along a direction substantially parallel to the reference axis 56 (FIG. 1). The resonance beam 102 may be mounted to the armature 50 as illustrated in FIG. 1.

Step 308 may comprise generating a shock pulse 54 (FIG. 1) at the shaker 40 (FIG. 1) in response to application of the amplified signal waveform to the shaker 40. The shock pulse 54 is generated by the reciprocative movement of the armature 50 (FIG. 1) in response to the alternating current flowing in the armature 50. The armature 50 may reciprocate at a frequency that may correspond to the frequency of the alternating current of the amplified signal waveform.

Step 310 may comprise orienting the shock pulse 54 (FIG. 1) substantially parallel to the reference axis 56 (FIG. 1). In this regard, the orientation of the shock pulse 54 corresponds to the orientation of the movement of the armature 50 (FIG. 1). As illustrated, the shaker 40 may be configured such that the armature 50 moves axially relative to the field coil 48 (FIG. 1). The resonance beam 102 (FIG. 1) is preferably attached to the armature 50 such that the resonance beam 102 and armature 50 remain in continuous contact at least for the duration of the shock pulse 54.

Step 312 may comprise exciting the resonance beam 102 (FIG. 1) into at least one resonance mode in response to generation of the shock pulse 54. The resonance mode may comprise a longitudinal mode, a bending or flexural mode, a torsional mode, or other modes or combinations thereof. The mode of excitation may be determined by a number of factors including, but not limited to, the configuration of the resonance beam 102 and/or the position, orientation and location of the resonance beam 102 relative to the shaker 40 (FIG. 1).

Step 314 may comprise magnifying the shock pulse 54 (FIG. 1) in the resonance beam 102 (FIG. 1) in response to excitation of the resonance beam 102. The shock pulse 54 may be magnified such that at least one location on the resonance beam 102 has a measured peak acceleration 206 (FIG. 14) that is greater than the measured peak acceleration 206 at a base portion 106 (FIG. 1) of the resonance beam 102. As indicated earlier, the shock pulse 54 may be magnified at the location of an anti-node (not shown) of the resonance beam 102.

Step 316 may comprise measuring the acceleration at a location on the resonance beam 102 (FIG. 1) in response to the shock pulse 54 (FIG. 1) and identifying one or more locations on the resonance beam 102 where the shock pulse 54 is magnified. The level of magnification at each location may be measured and compared to the measured acceleration at the base portion 106 (FIG. 1).

Step 318 may comprise calculating a simulated SRS 218 (FIG. 15) exhibited at each measured location. The simulated SRS 218 at each location may be calculated based on the measured peak acceleration 206 (FIG. 14) at the location. The simulated SRS 218 at each location may be compared to the desired SRS 208 (FIG. 15). As indicated above, the desired SRS 208 may represent the response of a service environment (e.g., a simulated or actual structure) to pyrotechnic shock generated with explosives.

Step 320 may comprise adjusting one or more test variables until one or more resonance beam 102 (FIG. 1) locations have been identified with a desired level of magnification of the shock pulse 54 (FIG. 1). In this regard, one or more locations may be identified where an absolute peak acceleration 224 (FIG. 15) of the simulated SRS 218 (FIG. 15) is substantially equivalent to the acceleration corresponding to the knee frequency 216 (FIG. 15) of the desired SRS 208 (FIG. 15). As noted above, the knee frequency 216 of the desired SRS 208 may correspond to the dominant frequency of the service environment in response to a pyrotechnic shock. By matching the absolute peak acceleration 224 to the acceleration at the knee frequency 216, the location on the resonance beam 102 may provide a relatively close simulation of the pyrotechnic shock to which an article may be subjected in actual service.

Test variables that may be adjusted may include the locations on the resonance beam 102 (FIG. 1) where acceleration is measured. As discussed above, different locations on a given resonance beam 102 embodiment may exhibit different levels of magnification. A resonance beam 102 may be mapped or surveyed by mounting accelerometers 62 (FIG. 1) at different locations on the resonance beam 102, subjecting the resonance beam 102 to a shock pulse 54 (FIG. 1), and measuring the magnification at each location until a location is identified having a desired magnification level. The simulated SRS 218 (FIG. 15) may also be calculated for each location based on the measured acceleration. Locations may be identified where the simulated SRS 218 is substantially equivalent to the desired SRS 208 (FIG. 15). In this regard, locations may be identified where the absolute peak acceleration 224 (FIG. 15) of the simulated SRS 218 is substantially equivalent to the acceleration corresponding to the knee frequency 216 of the desired SRS 208. Preferably the absolute peak acceleration 224 of the simulated SRS 218 is within the specified tolerance band 214 of the desired SRS 208.

The test variables may also comprise altering the configuration of the resonance beam 102 (FIG. 1) including altering the beam shape, beam geometry and/or the beam dimensions. In this regard, different configurations of the resonance beam 102 may be mounted to the shaker 40 (FIG. 1) to determine the response of each resonance beam 102 to a given shock pulse 54 (FIG. 1). A beam configuration may be selected based on the desired level of magnification and the quality of the simulated SRS 218 (FIG. 15). The quality of the SRS may include the magnitude of deviations of the simulated SRS 218 from the nominal straight-line of the desired SRS 208 (FIG. 15) and whether a substantial portion of the spectrum of the simulated SRS 218 (FIG. 15) is within the specified tolerance band 214 (FIG. 15). The test variables may also comprise altering the material from which the resonance beam 102 is formed. In this regard, material may be selected based on the relative stiffness or rigidity provided by the material. For example, material may be selected based upon the tensile modulus, the shear modulus, Poisson's ratio, or other mechanical properties.

The transient signal waveform may be adjusted to minimize the difference between the absolute peak acceleration 224 (FIG. 15) of the simulated SRS 218 (FIG. 15) and the acceleration at the knee frequency 216 (FIG. 15). For example, the amplification level of the transient signal waveform may be adjusted by adjusting the electrical power amplifier 28 (FIG. 1). The signal conditioning device 14 (FIG. 1) may also be adjusted to manipulate the transient signal waveform provided to the signal generator 12 (FIG. 1). For example, the analog filter 16 (FIG. 1) and/or the digital filter 18 (FIG. 1) may be adjusted to alter the magnitude of the transient signal at one or more frequencies as discussed above.

One or more of the above-mentioned test variables may be adjusted until the simulated SRS 218 (FIG. 15) is within a specified tolerance band (e.g., +/−6 dB, +/−3 dB, +9/−6 dB, etc.) of the desired SRS 208 (FIG. 15). Preferably, the test variables may be adjusted until the simulated SRS 218 is substantially equivalent to the desired SRS 208 at a knee frequency 216 (FIG. 15) of the desired SRS 208. The test variables may be adjusted until at least one location on the resonance beam 102 (FIG. 1) exhibits a simulated SRS 218 having an absolute peak acceleration 224 that is substantially equivalent to the acceleration to the knee frequency 216 of the desired SRS 208. In an embodiment, the test variables may be adjusted until at least one location on the resonance beam 102 exhibits a simulated SRS 218 having an absolute peak acceleration 224 of greater than a predetermined magnitude such as greater than approximately 5000 g's, greater than approximately 20,000 g's, or higher. The test variables may also be adjusted such that at least one location on the resonance beam 102 exhibits a simulated SRS 218 having spectral content of greater than approximately 100 kHz.

The above-discussed steps of measuring the response at a location on the resonance beam 102 (FIG. 1) may be performed with a mass model 152 (FIG. 1) mounted to the resonance beam 102 at the measuring location. As indicated earlier, the mass model 152 may have a mass and a mass distribution that may be substantially equivalent to the mass and mass distribution of the article under test 150 (FIG. 1). Upon identifying one or more locations on the resonance beam 102 that exhibit the desired response, the mass model 152 may be replaced by the article under test 150. The article under test 150 may be mounted at the location and may be subjected to a series of shock pulses 54 (FIG. 1). The article under test 150 may be successively tested in different orientation until the article is tested in each one of the three mutually perpendicular (i.e., x, y, z) axes.

In this regard, one or more triaxial accelerometers 62 (FIG. 1) may be mounted on the resonance beam 102 (FIG. 1) or on the holding fixture 154 (FIG. 1) mounted to the resonance beam 102. The accelerometers 62 are preferably mounted proximate to the article under test 150 (FIG. 1) and are positioned in non-contacting relation to the article under test 150. The article under test 150 may then be subjected to one or more shock pulses depending upon the purpose of the test. For example, during qualification testing, the article under test 150 may be subjected to three shocks per direction (i.e., +/−) for each axis (i.e., x, y, z) of the test article 150 for a total of 18 shocks. For flight acceptance testing, the article under test 150 may be subjected to a single shock in each direction (i.e., +/−) for each axis (i.e., x, y, z) for a total of 6 shocks. The article under test 150 may be assessed for damage and/or malfunction after each shock or after a series of shocks.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A system for simulating a pyrotechnic shock having a desired shock response spectrum (SRS), comprising:
   an electrical power amplifier configured to amplify a transient signal waveform representing the desired SRS, the desired SRS representing a spectrum of the transient signal at different frequencies;
   a shaker configured to generate a shock pulse in response to the amplified signal waveform; and
   a resonance beam mounted to the shaker and being configured to magnify the shock pulse.

2. The system of claim 1 wherein:
   the desired SRS has a knee frequency and an acceleration corresponding to the knee frequency; and
   the resonance beam being configured such that at least one location thereon exhibits a simulated SRS having an absolute peak acceleration that is substantially equivalent to the acceleration corresponding to the knee frequency.

3. The system of claim 1 wherein:
   the shaker has a reference axis;
   the shock pulse being oriented along a direction substantially parallel to the reference axis; and
   the resonance beam comprising an axial beam having a long axis oriented substantially parallel to the reference axis.

4. The system of claim 3 wherein:
   the axial beam has a height $h_A$ measured parallel to the long axis and a width $w_A$ measured perpendicular to the long axis; and
   the height $h_A$ being greater than the width $w_A$.

5. The system of claim 1 wherein:
   the shaker has a reference axis;
   the shock pulse being oriented predominantly along a direction parallel to the reference axis; and
   the resonance beam comprising a transverse beam having a long axis oriented substantially perpendicular to the reference axis.

6. The system of claim 5 wherein:
   the transverse beam has a height $h_T$ measured perpendicular to the long axis and a width $w_T$ measured parallel the long axis; and
   the width $w_T$ being greater than the height $h_T$.

7. The system of claim 6 wherein:
   the shaker has an armature having a perimeter;
   the transverse beam has opposing beam ends; and
   the width $w_T$ being such that at least one of the beam ends extends beyond the armature perimeter.

8. The system of claim 1 wherein:
   the shaker has a reference axis;
   the resonance beam comprises an L-beam including:
      an axial beam mounted to the shaker and having a long axis oriented substantially parallel to the reference axis; and a lateral element extending laterally outwardly from the axial beam.

9. The system of claim 8 wherein:
the shaker is oriented such that the reference axis is approximately horizontal.

10. The system of claim 9 wherein:
the axial beam is slidably supported on a beam support.

11. A method of simulating a pyrotechnic shock having a desired shock response spectrum (SRS), comprising the steps of:
generating a shock pulse using a shaker having a resonance beam mounted thereto;
exciting the resonance beam in response to the shock pulse; and
magnifying the shock pulse in at least one location on the resonance beam in response to excitation of the resonance beam such that the at least one location exhibits a simulated SRS that is substantially equivalent to the desired SRS, the desired SRS representing a spectrum of a transient signal at different frequencies.

12. The method of claim 11 wherein the desired SRS has a knee frequency and an acceleration corresponding to the knee frequency, the step of magnifying the shock pulse comprising:
magnifying the shock pulse such that the simulated SRS has an absolute peak acceleration that is substantially equivalent to the acceleration corresponding to the knee frequency.

13. The method of claim 11 wherein the step of magnifying the shock pulse comprises:
magnifying the shock pulse such that at least one location on the resonance beam exhibits a simulated SRS having an absolute peak acceleration of greater than approximately 5000 G's.

14. The method of claim 11 wherein the step of magnifying the shock pulse comprises:
magnifying the shock pulse such that at least one location on the resonance beam exhibits a simulated SRS having an absolute peak acceleration of greater than approximately 20,000 G's.

15. The method of claim 11 wherein the step of magnifying the shock pulse comprises:
magnifying the shock pulse such that at least one location on the resonance beam exhibits a simulated SRS having acceleration response greater than approximately 100 kHz.

16. The method of claim 11 further comprising the steps of:
orienting the shock pulse along a reference axis of the shaker; and
configuring the resonance beam as an axial beam having a long axis oriented substantially parallel to the reference axis.

17. The method of claim 11 further comprising the steps of:
orienting the shock pulse along a reference axis of the shaker; and
configuring the resonance beam as a transverse beam having a long axis oriented substantially perpendicular to the reference axis.

18. The method of claim 11 wherein:
orienting the shock pulse along a reference axis of the shaker; and
configuring the resonance beam as an L-beam including:
an axial beam mounted to the shaker and having a long axis oriented substantially parallel to the reference axis; and
a lateral element extending laterally outwardly from the axial beam.

19. A method of simulating a pyrotechnic shock, the pyrotechnic shock having a desired shock response spectrum (SRS) including a knee frequency and an acceleration corresponding to the knee frequency, the method comprising the steps of:
generating a transient signal waveform representing the desired SRS;
amplifying the signal waveform;
applying the amplified signal waveform to an electrodynamic shaker having a resonance beam mounted thereto;
generating a shock pulse at the shaker in response to the amplified signal waveform;
orienting the shock pulse substantially parallel to a reference axis of the shaker;
exciting the resonance beam in response to generation of the shock pulse;
magnifying the shock pulse in the resonance beam in response to excitation of the resonance beam;
measuring a peak acceleration at a location on the resonance beam in response to magnification of the shock pulse;
calculating a simulated SRS exhibited based on the measured peak acceleration; and
adjusting at least one of the following test variables until an absolute peak acceleration of the simulated SRS is substantially equivalent to the acceleration corresponding to the knee frequency:
a location on the resonance beam;
a configuration of the resonance beam.

* * * * *